(12) United States Patent
De Corte et al.

(10) Patent No.: US 8,530,655 B2
(45) Date of Patent: *Sep. 10, 2013

(54) HIV REPLICATION INHIBITING PYRIMIDINES

(75) Inventors: Bart De Corte, Southampton, PA (US); Marc René de Jonge, Hontenissestraat (NL); Jan Heeres, Vosselaar (BE); Chih Yung Ho, Lansdale, PA (US); Paul Adriaan Jan Janssen, Vosselaar (BE); Frank Xavier Jozef Herwig Arts, legal representative, Brasschaat (BE); Robert W. Kavash, Glenside, PA (US); Lucien Maria Henricus Koymans, Retie (BE); Michael Joseph Kukla, Maple Glen, PA (US); Donald William Ludovici, Quakertown, PA (US); Koen Jeanne Alfons Van Aken, Kuurne (BE); Koenraad Jozef Lodewijk Marcel Andries, Beerse (BE)

(73) Assignee: Janssen Pharmaceutica NV, Beerse (BE)

( * ) Notice: Subject to any disclaimer, the term of this patent is extended or adjusted under 35 U.S.C. 154(b) by 0 days.

This patent is subject to a terminal disclaimer.

(21) Appl. No.: 13/177,188

(22) Filed: Jul. 6, 2011

(65) Prior Publication Data

US 2011/0263625 A1 Oct. 27, 2011

Related U.S. Application Data

(63) Continuation of application No. 11/930,835, filed on Oct. 31, 2007, now Pat. No. 8,003,789, which is a continuation of application No. 11/204,513, filed on Aug. 16, 2005, now abandoned, which is a continuation of application No. 10/634,682, filed on Aug. 5, 2003, now Pat. No. 7,037,917, which is a continuation of application No. 09/430,966, filed on Nov. 1, 1999, now Pat. No. 6,878,717.

(60) Provisional application No. 60/107,792, filed on Nov. 10, 1998, provisional application No. 60/143,962, filed on Jul. 15, 1999.

(30) Foreign Application Priority Data

Sep. 24, 1999 (WO) .................. PCT/EP99/07417

(51) Int. Cl.
C07D 401/12 (2006.01)
C07D 403/12 (2006.01)
A61K 31/506 (2006.01)
A61P 31/18 (2006.01)

(52) U.S. Cl.
USPC ............ 544/321; 544/323; 544/324; 544/332

(58) Field of Classification Search
USPC .................. 544/321, 323, 324, 332; 514/269, 514/272, 275

See application file for complete search history.

(56) References Cited

U.S. PATENT DOCUMENTS 3,459,731 A 8/1969 Gramera et al.
4,659,363 A 4/1987 Hubele et al.
(Continued)

FOREIGN PATENT DOCUMENTS

EP 0135472 B1 7/1984
EP 0588762 A1 8/1993
(Continued)

OTHER PUBLICATIONS

Arnold, E., 21th European Crystallographic Meeting, Durban, South Africa, Aug. 27, 2003.

(Continued)

*Primary Examiner* — Venkataraman Balasubramanian
(74) *Attorney, Agent, or Firm* — Michael J. Atkins

(57) ABSTRACT

This invention concerns the use of compounds of formula

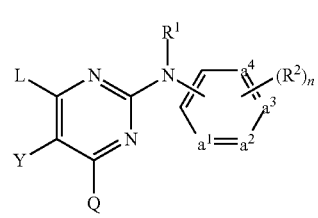

(I)

the N-oxides, the pharmaceutically acceptable addition salts, quaternary amines and the stereochemically isomeric forms thereof, wherein $-a^1=a^2-a^3=a^4-$ forms a phenyl, pyridinyl, pyrimidinyl, pyridazinyl or pyrazinyl with the attached vinyl group; n is 0 to 4; and where possible 5; $R^1$ is hydrogen, aryl, formyl, $C_{1-6}$alkylcarbonyl, $C_{1-6}$alkyl, $C_{1-6}$alkyloxycarbonyl, substituted $C_{1-6}$alkyl, or substituted $C_{1-6}$alkyloxy$C_{1-6}$alkylcarbonyl; each $R^2$ independently is hydroxy, halo, optionally substituted $C_{1-6}$alkyl, $C_{2-6}$alkenyl or $C_{2-6}$alkynyl, $C_{3-7}$cycloalkyl, $C_{1-6}$alkyloxy, $C_{1-6}$alkyloxycarbonyl, carboxyl, cyano, nitro, amino, mono- or di($C_{1-6}$alkylamino, polyhalomethyl, polyhalomethyloxy, polyhalomethylthio, $-S(=O)_pR^6$, $-NH-S(=O)_pR^6$, $-C(=O)R^6$, $-NHC(=O)H$, $-C(=O)NHNH_2$, $-NHC(=O)R^6$, $-C(=NH)R^6$ or a 5-membered heterocyclic ring; p is 1 or 2; L is optionally substituted $C_{1-10}$alkyl, $C_{2-10}$alkenyl, $C_{2-10}$alkynyl or $C_{3-7}$cycloalkyl; or L is $-X-R^3$ wherein $R^3$ is optionally substituted phenyl, pyridinyl, pyrimidinyl, pyrazinyl or pyridazinyl; X is $-NR^1-$, $-NH-NH-$, $-N=N-$, $-O-$, $-C(=O)-$, $-CHOH-$, $-S-$, $-S(=O)-$ or $-S(=O)_2-$; Q is hydrogen, $C_{1-6}$alkyl, halo, polyhalo-$C_{1-6}$alkyl or an optionally substituted amino group; Y represents hydroxy, halo, $C_{3-7}$cycloalkyl, optionally substituted $C_{1-6}$alkyl, $C_{2-6}$alkenyl or $C_{2-6}$alkynyl, $C_{1-6}$alkyloxy, $C_{1-6}$alkyloxycarbonyl, carboxyl, cyano, nitro, amino, mono- or di($C_{1-6}$alkyl)amino, polyhalomethyl, polyhalomethyloxy, polyhalomethylthio, $-S(=O)_pR^6$, $-NH-S(=O)_pR^6$, $-C(=O)R^6$, $-NHC(=O)H$, $-C(=O)NHNH_2$, $-NHC(=O)R^6$, $-C(=NH)R^6$ or aryl; aryl is optionally substituted phenyl; Het is an optionally substituted heterocyclic radical; for the manufacture of a medicine for the treatment of subjects suffering from HIV (Human Immunodeficiency Virus) infection.

10 Claims, No Drawings

(56) References Cited

U.S. PATENT DOCUMENTS

| | | | |
|---|---|---|---|
| 4,694,009 A | 9/1987 | Hubele et al. | |
| 5,017,466 A | 5/1991 | Kobayashi et al. | |
| 5,691,364 A | 11/1997 | Buckman et al. | |
| 6,048,866 A | 4/2000 | Hutchings et al. | |
| 6,093,716 A | 7/2000 | Davis et al. | |
| 6,197,779 B1 | 3/2001 | Andries et al. | |
| 6,200,977 B1 | 3/2001 | Cushing et al. | |
| 6,528,513 B2 | 3/2003 | Cushing et al. | |
| 6,835,726 B2 | 12/2004 | Cushing et al. | |
| 6,878,717 B2* | 4/2005 | De Corte et al. | 514/269 |
| 7,763,631 B2* | 7/2010 | Kukla et al. | 514/275 |
| 8,003,789 B2* | 8/2011 | De Corte et al. | 544/321 |
| 8,026,248 B2* | 9/2011 | Andries et al. | 514/275 |

FOREIGN PATENT DOCUMENTS

| | | |
|---|---|---|
| EP | 0371139 B1 | 10/1994 |
| EP | 0834507 B1 | 4/1998 |
| EP | 0945442 A1 | 5/1998 |
| EP | 0945443 B1 | 9/1999 |
| WO | WO 95/10506 A1 | 4/1995 |
| WO | WO 97/18839 A1 | 5/1997 |
| WO | WO 97/19065 A1 | 5/1997 |
| WO | WO 98/41512 A1 | 9/1998 |

OTHER PUBLICATIONS

Das, K., et al. "Could Multiple Modes of Binding of a Potent NNRTI TMC125-R165335 Explain its Potency Against common Drug-Resistant Mutants?", 10th Conference on Retroviruses and Opportunistic Infection, Session 72 Poster Presentations (2003).

Furukawa, M., et al. "Syntheses of Compounds Related to Guanidine and Their Inhibitory Action of Growth of HeLa Cells", Chem. Pharm. Bull, vol. 9 (1961) pp. 914-921.

Gazzard, B., et al. "TMC125, a Next-Generation NNRTI1, Demonstrates High Potency After 7 Days Therapy in Treatment-Experienced HIV-1-Infected Individuals with Phenotypic NNRTI", CROI, Seattle, Feb. 2002 Session 4.

Gazzard, B., et al. "An Open-Label Assessment of TMC 125—a New, Next-Generation NNRTI, for 7 Days in HIV-1 Infected Individuals with NNRTI Resistance", AIDS (2003) vol. 17, pp. 49-54 Fast Track.

Gazzard, B., et al. "TMC125, a Next Generation NNRT! Demonstrates High Potency After 7 Days Therapy in Treatment-Experienced HIV-1 Infected Individuals with Phenotypic NNRT1-Resistance" Poster No. TuPEB4392, XIV International AIDS Conference Jul. 7-11, 2002, Barcelona, Spain.

Gruzdev, B., et al. "A Randomized, Double-Blind, Placebo-Controlled Trial of TMC125 as 7-Day Monotherapy in Antiretroviral Naïve, HIV-1 Infected Subjects", AIDS (2003) vol. 17, pp. 2487-2492.

Gulick, R., "New Antiretroviral Drugs", Clinical Microbiology and Infectious Diseases (2003) vol. 9, pp. 186-193.

Koyanagi, Y., et al. "Selective Cytotoxicity of AIDS Virus Infection Towards HTLV-I-Transformed Cell Lines", Int. J. Cancer, vol. 36 (1985) pp. 445-451.

Ludovici, D., et al. "Evolution of Anti-HIV Drug Candidates. Part 3: Diarylpyrimidine (DAPY) Analogues", Bioorganic & Medicinal Chemistry Letters, vol. 11 (2001) pp. 2235-2239.

McOmie, J., "Protective Groups in Organic Chemistry", (1973) Title Page and Table of Contents.

Nógrádi, M., "Dimethyl-β-Cyclodextrin", Drugs of the Future, vol. 9, No. 8, (1984), pp. 577-578.

Pauwels, R., et al. "Potent and Highly Selective Human Immunodeficiency Virus Type 1 (HIV-1) Inhibition by a Series of α-anilinophenylacetamide Derivatives Targeted at HIV-1 Reverse Transcriptase", Proc. Natl. Acad. Sci, USA vol. 90, (1993) pp. 1711-1715.

Sankatsing, S., et al. "TMIC125 Monotherapy for 1 Week Results in a Similar Initial Rate of Decline of HIV-1 RNA As Therapy with a 5-Drug Regimen", (2002), Abstract: Antiretroviral Chemotherapy: New Agents, Session 4: Oral Abstract Sessions.

Sankatsing, S., et al. "TMC125 Exerts Similar Initial Antiviral Potency as a Five-Drug, Triple class Antiretroviral Regimen", AIDS (2003) vol. 17 pp. 2623-2627.

T.W. Greene & P.G.M. Wutz (eds.), Protective Groups in Organic Synthesis, $2^{nd}$ edition, Wiley Interscience, (1991), pp. 473.

Udier-Blagovic, M., et al. "Validation of a Model for the Complex of HIV-1 Reverse Transcriptase with Nonnucleoside Inhibitor TMC125", J American Chemical Society (2003) vol. 125 pp. 6016-6017.

Vingerhoets, J., et al. "Antiviral Activity of TMC125, a Potent next-generationNNRT1 Against > 5000 Recombinant Clinical Isolates Exhibiting a Wide Range of (NNRT) Resistance", Poster, Jun. 2003, XIIth International HIV Drug Resistance Workshop, Cabo San Lucas, Mexico.

Vingerhoets, J., et al. "Characterization of Resistance Before and After short-Term Therapy with TMC125 in Patients with Documented NNRTI Resistance", XIIth International HIV Drug resistance Workshop, Jun. 10-14, 2003, Mexico.

Vingerhoets, J., et al. "Antiviral Activity of TMC125 Against a Panel of Site-Directed Mutants Encompassing Mutations Observed in vitro and in vivo", 11th Conference on Retroviruses and Opportunistic, Feb. 2004.

International Search Report mailed Feb. 2, 2000 for related International Application No. PCT/EP1999/07417.

\* cited by examiner

HIV REPLICATION INHIBITING PYRIMIDINES

CROSS REFERENCE TO RELATED APPLICATIONS

This application is a continuation of U.S. Ser. No. 11/930,835, filed Oct. 31, 2007 now U.S. Pat. No. 8,003,789, which is a continuation of U.S. Ser. No. 11/204,513, filed Aug. 16, 2005 now abandoned, which is a continuation of U.S. Ser. No. 10/634,682, filed Aug. 5, 2003, now U.S. Pat. No. 7,037,917, which is a continuation of U.S. Ser. No. 09/430,966, filed Nov. 1, 1999, now U.S. Pat. No. 6,878,717, which claims priority to applications U.S. Provisional Application No. 60/107,792, filed Nov. 10, 1998 and U.S. Provisional Application No. 60/143,962, filed Jul. 15, 1999 and PCT/EP1999/07417, filed Sep. 24, 1999, the entire disclosures of which are hereby incorporated in their entirety.

The present invention concerns the use of pyrimidine derivatives having Human Immunodeficiency Virus (HIV) replication inhibiting properties. It also relates to a novel group of pyrimidine derivatives, their use as a medicine, their processes for preparation and pharmaceutical compositions comprising them.

EP-0,834,507 discloses substituted diamino 1,3,5-triazine derivatives having HIV replication inhibiting properties. The present compounds differ from the known 1,3,5-triazines by structure and by their improved HIV replication inhibiting properties.

The present invention is concerned with the use of compounds of formula (I)

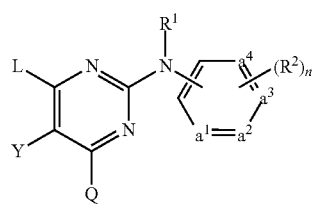

the N-oxides, the pharmaceutically acceptable addition salts, the quaternary amines and the stereochemically isomeric forms thereof, wherein
$-a^1=a^2-a^3=a^4-$ represents a bivalent radical of formula $$-CH=CH-CH=CH- \quad (a-1);$$

$$-N=CH-CH=CH- \quad (a-2);$$

$$-N=CH-N=CH- \quad (a-3);$$

$$-N=CH-CH=N- \quad (a-4);$$

$$-N=N-CH=CH- \quad (a-5);$$

n is 0, 1, 2, 3 or 4; and in case $-a^1=a^2-a^3=a^4-$ is (a-1), then n may also be 5;
$R^1$ is hydrogen; aryl; formyl; $C_{1-6}$alkylcarbonyl; $C_{1-6}$alkyl; $C_{1-6}$alkyloxycarbonyl; $C_{1-6}$alkyl substituted with formyl, $C_{1-6}$alkylcarbonyl, $C_{1-6}$alkyloxycarbonyl, $C_{1-6}$alkylcarbonyloxy; $C_{1-6}$alkyloxy$C_{1-6}$alkylcarbonyl substituted with $C_{1-6}$alkyloxycarbonyl;
each $R^2$ independently is hydroxy, halo, $C_{1-6}$alkyl optionally substituted with cyano or $-C(=O)R^6$, $C_{3-7}$cycloalkyl, $C_{2-6}$alkenyl optionally substituted with one or more halogen atoms or cyano, $C_{2-6}$alkynyl optionally substituted with one or more halogen atoms or cyano, $C_{1-6}$alkyloxy, $C_{1-6}$alkyloxycarbonyl, carboxyl, cyano, nitro, amino, mono- or di($C_{1-6}$alkyl)amino, polyhalomethyl, polyhalomethyloxy, polyhalomethylthio, $-S(=O)_pR^6$, $-NH-S(=O)_pR^6$, $-C(=O)R^6$, $-NHC(=O)H$, $C(=O)NHNH_2$, $-NHC(=O)R^6$, $-C(=NH)R^6$ or a radical of formula

wherein each A independently is N, CH or $CR^6$;
B is NH, O, S or $NR^6$;
p is 1 or 2; and
$R^6$ is methyl, amino, mono- or dimethylamino or polyhalomethyl;
L is $C_{1-10}$alkyl, $C_{2-10}$alkenyl, $C_{2-10}$alkynyl, $C_{3-7}$cycloalkyl, whereby each of said aliphatic group may be substituted with one or two substituents independently selected from
  $C_{3-7}$cycloalkyl,
  indolyl or isoindolyl, each optionally substituted with one, two, three or four substituents each independently selected from halo, $C_{1-6}$alkyl, hydroxy, $C_{1-6}$alkyloxy, cyano, aminocarbonyl, nitro, amino, polyhalomethyl, polyhalomethyloxy and $C_{1-6}$alkylcarbonyl,
  phenyl, pyridinyl, pyrimidinyl, pyrazinyl or pyridazinyl, wherein each of said aromatic rings may optionally be substituted with one, two, three, four or five substituents each independently selected from the substituents defined in $R^2$; or
L is $-X-R^3$ wherein
  $R^3$ is phenyl, pyridinyl, pyrimidinyl, pyrazinyl or pyridazinyl, wherein each of said aromatic rings may optionally be substituted with one, two, three, four or five substituents each independently selected from the substituents defined in $R^2$; and
  X is $-NR^1-$, $-NH-NH-$, $-N=N-$, $-O-$, $-C(=O)-$, $-CHOH-$, $-S-$, $-S(=O)-$ or $-S(=O)_2-$;
Q represents hydrogen, $C_{1-6}$alkyl, halo, polyhalo$C_{1-6}$alkyl or $-NR^4R^5$; and
$R^4$ and $R^5$ are each independently selected from hydrogen, hydroxy, $C_{1-12}$alkyl, $C_{1-12}$alkyloxy, $C_{1-12}$alkylcarbonyl, $C_{1-12}$alkyloxycarbonyl, aryl, amino, mono- or di($C_{1-12}$alkyl)amino, mono- or di($C_{1-12}$alkyl)aminocarbonyl wherein each of the aforementioned $C_{1-12}$alkyl groups may optionally and each individually be substituted with one or two substituents each independently selected from hydroxy, $C_{1-6}$alkyloxy, hydroxy$C_{1-6}$alkyloxy, carboxyl, $C_{1-6}$alkyloxycarbonyl, cyano, amino, imino, mono- or di($C_{1-6}$alkyl)amino, polyhalomethyl, polyhalomethyloxy, polyhalomethylthio, $-S(=O)_pR^6$, $-NH-S(=O)_pR^6$, $-C(=O)R^6$, $-NHC(=O)H$, $-C(=O)NHNH_2$, $-NHC(=O)R^6$, $-C(=NH)R^6$, aryl and Het; or
$R^4$ and $R^5$ taken together may form pyrrolidinyl, piperidinyl, morpholinyl, azido or mono- or di($C_{1-12}$alkyl)amino$C_{1-4}$alkylidene;
Y represents hydroxy, halo, $C_{3-7}$cycloalkyl, $C_{2-6}$alkenyl optionally substituted with one or more halogen atoms, $C_{2-6}$alkynyl optionally substituted with one or more halogen atoms, C$_{1-6}$alkyl substituted with cyano or —C(=O)R$^6$, C$_{1-6}$alkyloxy, C$_{1-6}$alkyloxycarbonyl, carboxyl, cyano, nitro, amino, mono- or di(C$_{1-6}$alkyl)amino, polyhalomethyl, polyhalomethyloxy, polyhalomethylthio, —S(=O)$_p$R$^6$, —NH—S(=O)$_p$R$^6$, —C(=O)R$^6$, —NHC(=O)H, —C(=O)NHNH$_2$, —NHC(=O)R$^6$, —C(=NH)R$^6$ or aryl;

aryl is phenyl or phenyl substituted with one, two, three, four or five substituents each independently selected from halo, C$_{1-6}$alkyl, C$_{3-7}$cycloalkyl, C$_{1-6}$alkyloxy, cyano, nitro, polyhaloC$_{1-6}$alkyl and polyhaloC$_{1-6}$alkyloxy;

Het is an aliphatic or aromatic heterocyclic radical; said aliphatic heterocyclic radical is selected from pyrrolidinyl, piperidinyl, homopiperidinyl, piperazinyl, morpholinyl, tetrahydrofuranyl and tetrahydrothienyl wherein each of said aliphatic heterocyclic radical may optionally be substituted with an oxo group; and said aromatic heterocyclic radical is selected from pyrrolyl, furanyl, thienyl, pyridinyl, pyrimidinyl, pyrazinyl and pyridazinyl wherein each of said aromatic heterocyclic radical may optionally be substituted with hydroxy;

for the manufacture of a medicine for the treatment of subjects suffering from HIV (Human Immunodeficiency Virus) infection.

The present invention also relates to a method of treating warm-blooded animals suffering from HIV (Human Immunodeficiency Virus) infection. Said method comprises the administration of a therapeutically effective amount of a compound of formula (I) or a N-oxide form, a pharmaceutically acceptable addition salt or a stereochemically isomeric form thereof in admixture with a pharmaceutical carrier.

This invention also relates to novel compounds having the formula

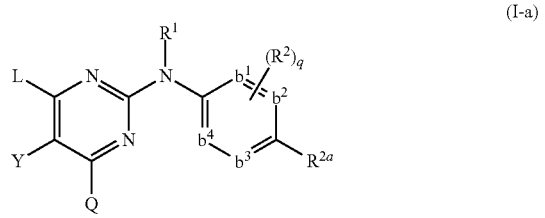

(I-a)

the N-oxides, the addition salts, the quaternary amines and the stereochemically isomeric forms thereof, wherein -b$^1$=b$^2$-C(R$^{2a}$)=b$^3$-b$^4$= represents a bivalent radical of formula

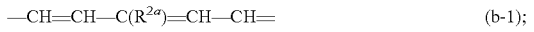       (b-1);

       (b-2);

       (b-3);

       (b-4);

       (b-5);

       (b-6);

       (b-7);

q is 0, 1, 2; or where possible q is 3 or 4;

R$^1$ is hydrogen; aryl; formyl; C$_{1-6}$alkylcarbonyl; C$_{1-6}$alkyl; C$_{1-6}$alkyloxycarbonyl; C$_{1-6}$alkyl substituted with formyl, C$_{1-6}$alkylcarbonyl, C$_{1-6}$alkyloxycarbonyl, C$_{1-6}$alkylcarbonyloxy, C$_{1-6}$alkyloxyC$_{1-6}$alkylcarbonyl substituted with C$_{1-6}$alkyloxycarbonyl R$^{2a}$ is cyano, aminocarbonyl, mono- or di(methyl)aminocarbonyl, C$_{1-6}$alkyl substituted with cyano, aminocarbonyl or mono- or di(methyl)aminocarbonyl, C$_{2-6}$alkenyl substituted with cyano, or C$_{2-6}$alkynyl substituted with cyano;

each R$^2$ independently is hydroxy, halo, C$_{1-6}$alkyl optionally substituted with cyano or —C(=O)R$^6$, C$_{3-7}$cycloalkyl, C$_{2-6}$alkenyl optionally substituted with one or more halogen atoms or cyano, C$_{2-6}$alkynyl optionally substituted with one or more halogen atoms or cyano, C$_{1-6}$alkyloxy, C$_{1-6}$alkyloxycarbonyl, carboxyl, cyano, nitro, amino, mono- or di(C$_{1-6}$alkyl)amino, polyhalomethyl, polyhalomethyloxy, polyhalomethylthio, —S(=O)$_p$R$^6$, —NH—S(=O)$_p$R$^6$, —C(=O)R$^6$, —NHC(=O)H, —C(=O)NHNH$_2$, —NHC(=O)R$^6$, —C(=NH)R$^6$ or a radical of formula

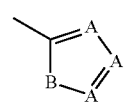

(c)

wherein each A independently is N, CH or CR$^6$;

B is NH, O, S or NR$^6$;

p is 1 or 2; and

R$^6$ is methyl, amino, mono- or dimethylamino or polyhalomethyl;

L is C$_{1-10}$alkyl, C$_{2-10}$alkenyl, C$_{2-10}$alkynyl, C$_{3-7}$cycloalkyl, whereby each of said aliphatic group may be substituted with one or two substituents independently selected from C$_{3-7}$cycloalkyl, indolyl or isoindolyl, each optionally substituted with one, two, three or four substituents each independently selected from halo, C$_{1-6}$alkyl, hydroxy, C$_{1-6}$alkyloxy, cyano, aminocarbonyl, nitro, amino, polyhalomethyl, polyhalomethyloxy and C$_{1-6}$alkylcarbonyl, phenyl, pyridinyl, pyrimidinyl, pyrazinyl or pyridazinyl, wherein each of said aromatic rings may optionally be substituted with one, two, three, four or five substituents each independently selected from the substituents defined in R$^2$; or L is —X—R$^3$ wherein R$^3$ is phenyl, pyridinyl, pyrimidinyl, pyrazinyl or pyridazinyl, wherein each of said aromatic rings may optionally be substituted with one, two, three, four or five substituents each independently selected from the substituents defined in R$^2$; and X is —NR$^1$—, —NH—NH—, —N=N—, —O—, —C(=O)—, —CHOH—, —S—, —S(=O)— or —S(=O)$_2$—;

Q represents hydrogen, C$_{1-6}$alkyl, halo, polyhaloC$_{1-6}$alkyl or —NR$^4$R$^5$; and R$^4$ and R$^5$ are each independently selected from hydrogen, hydroxy, C$_{1-12}$alkyl, C$_{1-12}$alkyloxy, C$_{1-12}$alkylcarbonyl, C$_{1-12}$alkyloxycarbonyl, aryl, amino, mono- or di(C$_{1-12}$alkyl)amino, mono- or di(C$_{1-12}$alkyl)aminocarbonyl wherein each of the aforementioned C$_{1-12}$alkyl groups may optionally and each individually be substituted with one or two substituents each independently selected from hydroxy, C$_{1-6}$alkyloxy, hydroxyC$_{1-6}$alkyloxy, carboxyl, C$_{1-6}$alkyloxycarbonyl, cyano, amino, imino, mono- or di($C_{1-6}$alkyl)amino, polyhalomethyl, polyhalomethyloxy, polyhalomethylthio, —S(=O)$_p$R$^6$, —NH—S(=O)$_p$R$^6$, —C(=O)R$^6$, —NHC(=O)H, —C(=O)NHNH$_2$, —NHC(=O)R$^6$, —C(=NH)R$^6$, aryl and Het; or R$^4$ and R$^5$ taken together may form pyrrolidinyl, piperidinyl, morpholinyl, azido or mono- or di($C_{1-12}$alkyl)amino$C_{1-4}$alkylidene;

Y represents hydroxy, halo, $C_{3-7}$cycloalkyl, $C_{2-6}$alkenyl optionally substituted with one or more halogen atoms, $C_{2-6}$alkynyl optionally substituted with one or more halogen atoms, $C_{1-6}$alkyl substituted with cyano or —C(=O)R$^6$, $C_{1-6}$alkyloxy, $C_{1-6}$alkyloxycarbonyl, carboxyl, cyano, nitro, amino, mono- or di($C_{1-6}$alkyl)amino, polyhalomethyl, polyhalomethyloxy, polyhalomethylthio, —S(=O)$_p$R$^6$, —NH—S(=O)$_p$R$^6$, —C(=O)R$^6$, —NHC(=O)H, —C(=O)NHNH$_2$, —NHC(=O)R$^6$, —C(=NH)R$^6$ or aryl;

aryl is phenyl or phenyl substituted with one, two, three, four or five substituents each independently selected from halo, $C_{1-6}$alkyl, $C_{3-7}$cycloalkyl, $C_{1-6}$alkyloxy, cyano, nitro, polyhalo$C_{1-6}$alkyl and polyhalo$C_{1-6}$alkyloxy;

Het is an aliphatic or aromatic heterocyclic radical; said aliphatic heterocyclic radical is selected from pyrrolidinyl, piperidinyl, homopiperidinyl, piperazinyl, morpholinyl, tetrahydrofuranyl and tetrahydrothienyl wherein each of said aliphatic heterocyclic radical may optionally be substituted with an oxo group; and said aromatic heterocyclic radical is selected from pyrrolyl, furanyl, thienyl, pyridinyl, pyrimidinyl, pyrazinyl and pyridazinyl wherein each of said aromatic heterocyclic radical may optionally be substituted with hydroxy.

As used herein $C_{1-6}$alkyl as a group or part of a group defines straight or branched chain saturated hydrocarbon radicals having from 1 to 6 carbon atoms such as methyl, ethyl, propyl, 1-methylethyl, butyl, pentyl, hexyl, 2-methylpropyl, 2-methylbutyl and the like; $C_{1-10}$alkyl as a group or part of a group defines straight or branched chain saturated hydrocarbon radicals having from 1 to 10 carbon atoms such as the groups defined for $C_{1-6}$alkyl and heptyl, octyl, nonyl, decyl and the like; $C_{1-12}$alkyl as a group or part of a group defines straight or branched chain saturated hydrocarbon radicals having from 1 to 12 carbon atoms such as the groups defined for $C_{1-10}$alkyl and undecyl, dodecyl and the like; $C_{1-4}$alkylidene defines straight or branched chain saturated bivalent hydrocarbon radicals having from 1 to 4 carbon atoms such as methylene, 1,2-ethanediyl or 1,2-ethylidene, 1,3-propanediyl or 1,3-propylidene, 1,4-butanediyl or 1,4-butylidene and the like; $C_{3-7}$cycloalkyl is generic to cyclopropyl, cyclobutyl, cyclopentyl, cyclohexyl and cycloheptyl; $C_{2-6}$alkenyl defines straight and branched chain hydrocarbon radicals having from 2 to 6 carbon atoms containing a double bond such as ethenyl, propenyl, butenyl, pentenyl, hexenyl and the like; $C_{2-10}$alkenyl defines straight and branched chain hydrocarbon radicals having from 2 to 10 carbon atoms containing a double bond such as the groups defined for $C_{2-6}$alkenyl and heptenyl, octenyl, nonenyl, decenyl and the like; $C_{2-6}$alkynyl defines straight and branched chain hydrocarbon radicals having from 2 to 6 carbon atoms containing a triple bond such as ethynyl, propynyl, butyryl, pentynyl, hexynyl and the like; $C_{2-10}$alkynyl defines straight and branched chain hydrocarbon radicals having from 2 to 10 carbon atoms containing a triple bond such as the groups defined for $C_{2-6}$alkynyl and heptynyl, octynyl, nonynyl, decynyl and the like.

As used herein before, the term (=O) forms a carbonyl moiety when attached to a carbon atom, a sulfoxide group when attached once to a sulfur atom, and a sulfonyl group when attached twice to a sulfur atom.

The term halo is generic to Nora, chloro, bromo and iodo. As used in the foregoing and hereinafter, polyhalomethyl as a group or part of a group is defined as mono- or polyhalosubstituted methyl, in particular methyl with one or more fluoro atoms, for example, difluoromethyl or trifluoromethyl; polyhalo$C_{1-6}$alkyl as a group or part of a group is defined as mono- or polyhalosubstituted $C_{1-6}$alkyl, for example, the groups defined in halomethyl, 1,1-difluoro-ethyl and the like. In case more than one halogen atoms are attached to an alkyl group within the definition of polyhalomethyl or polyhalo$C_{1-6}$alkyl, they may be the same or different.

Het is meant to include all the possible isomeric forms of the heterocycles mentioned in the definition of Het, for instance, pyrrolyl also includes 2H-pyrrolyl.

The Het radical may be attached to the remainder of the molecule of formula (I) or (I-a) through any ring carbon or heteroatom as appropriate. Thus, for example, when the heterocycle is pyridinyl, it may be 2-pyridinyl, 3-pyridinyl or 4-pyridinyl.

When any variable (eg. aryl, R$^2$, R$^6$ etc.) occurs more than one time in any constituent, each definition is independent.

Lines drawn into ring systems from substituents indicate that the bond may be attached to any of the suitable ring atoms.

It will be appreciated that some of the compounds of formula (I) or (I-a) and their N-oxides, addition salts, quaternary amines and stereochemically isomeric forms may contain one or more centers of chirality and exist as stereochemically isomeric forms.

The term "stereochemically isomeric forms" as used hereinbefore defines all the possible stereoisomeric forms which the compounds of formula (I) or (I-a), and their N-oxides, addition salts, quaternary amines or physiologically functional derivatives may possess. Unless otherwise mentioned or indicated, the chemical designation of compounds denotes the mixture of all possible stereochemically isomeric forms, said mixtures containing all diastereomers and enantiomers of the basic molecular structure as well as each of the individual isomeric forms of formula (I) or (I-a) and their N-oxides, salts, solvates or quaternary amines substantially free, i.e. associated with less than 10%, preferably less than 5%, in particular less than 2% and most preferably less than 1% of the other isomers. In particular, stereogenic centers may have the R- or S-configuration; substituents on bivalent cyclic (partially) saturated radicals may have either the cis- or trans-configuration. Compounds encompassing double bonds can have an E or Z-stereochemistry at said double bond. Stereochemically isomeric forms of the compounds of formula (I) or (I-a) are obviously intended to be embraced within the scope of this invention.

For therapeutic use, salts of the compounds of formula (I) or (I-a) are those wherein the counterion is pharmaceutically acceptable. However, salts of acids and bases which are not pharmaceutically acceptable may also find use, for example, in the preparation or purification of a pharmaceutically acceptable compound. All salts, whether pharmaceutically acceptable or not are included within the ambit of the present invention.

The pharmaceutically acceptable acid and base addition salts as mentioned hereinabove are meant to comprise the therapeutically active non-toxic acid and base addition salt forms which the compounds of formula (I) or (I-a) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

Conversely said salt forms can be convened by treatment with an appropriate base into the free base form.

The compounds of formula (I) or (I-a) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term addition salt as used hereinabove also comprises the solvates which the compounds of formula (I) or (I-a) as well as the salts thereof, are able to form. Such solvates are for example hydrates, alcoholates and the like.

Some of the compounds of formula (I) or (I-a) may also exist in their tautomeric form. Such forms although not explicitly indicated in the above formula are intended to be included within the scope of the present invention.

Whenever used hereinafter, the term "compounds of formula (I)" or "compounds of formula (I-a)" is meant to include also the N-oxides, the addition salts, the quaternary amines and all stereoisomeric forms.

A special group of compounds contains those compounds of formula (I) wherein $R^1$ is hydrogen, aryl, formyl, $C_{1-6}$alkylcarbonyl, $C_{1-6}$alkyl, $C_{1-6}$alkyloxycarbonyl, $C_{1-6}$alkyl substituted with formyl, $C_{1-6}$alkylcarbonyl, $C_{1-6}$alkyloxycarbonyl.

Another special group of compounds contains those compounds of formula (I) wherein one or more of the following restrictions apply:
  i) -$a^1$=$a^2$-$a^3$=$a^4$- is a radical of formula (a-1);
  ii) $R^1$ is hydrogen;
  iii) n is 1;
  iv) $R^2$ is cyano, preferably in the para position relative to the —$NR^1$— group;
  v) Y is cyano, —C(=O)$NH_2$ or a halogen, preferably a halogen;
  vi) Q is hydrogen or —$NR^4R^5$ wherein $R^4$ and $R^5$ are preferably hydrogen;
  vii) L is —X—$R^3$ wherein X is preferably $NR^1$, O or S, most preferably X is NH, and $R^3$ is substituted phenyl with $C_{1-6}$alkyl, halogen and cyano as preferred substituents.

Still another special group of compounds contains those compounds of formula (I-a) wherein $R^1$ is hydrogen, aryl, formyl, $C_{1-6}$alkylcarbonyl, $C_{1-6}$alkyl, $C_{1-6}$alkyloxycarbonyl, $C_{1-6}$alkyl substituted with formyl, $C_{1-6}$alkylcarbonyl, $C_{1-6}$alkyloxycarbonyl.

Another special group of compounds contains also those compounds of formula (I-a) wherein one or more of the following restrictions apply:
  i) -$b^1$=$b^2$-C($R^{2a}$)=$b^3$-$b^4$= is a radical of formula (b-1);
  ii) q is 0;
  iii) $R^{2a}$ is cyano or —C(=O)$NH_2$, preferably $R^{2a}$ is cyano;
  iv) Y is cyano, —C(=O)$NH_2$ or a halogen, preferably a halogen;
  v) Q is hydrogen or —$NR^4R^5$ wherein $R^4$ and $R^5$ are preferably hydrogen;
  vi) L is —X—$R^3$ wherein X is preferably $NR^1$, O or S, most preferably X is NH, and $R^3$ is substituted phenyl with $C_{1-6}$alkyl, halogen and cyano as preferred substituents.

An interesting group of compounds are those compounds of formula (I) or (I-a) wherein L is —X—$R^3$ wherein $R^3$ is 2,4,6-trisubstituted phenyl, each substituent independently selected from chloro, bromo, fluoro, cyano or $C_{1-4}$alkyl.

Also interesting are those compounds of formula (I) or (I-a) wherein Y is chloro or bromo and Q is hydrogen or amino.

Particular compounds are those compounds of formula (I) or (I-a) wherein the moiety in the 2 position of the pyrimidine ring is a 4-cyano-anilino group.

Preferred compounds are those compounds of formula (I) or (I-a) wherein the moiety in the 2 position of the pyrimidine ring is a 4-cyano-anilino group, L is —X—$R^3$ wherein $R^3$ is a 2,4,6-trisubstituted phenyl, Y is a halogen and Q is hydrogen or $NH_2$.

Most preferred compounds are:

4-[[4-amino-5-chloro-6-[(2,4,6-trimethylphenyl)amino]-2-pyrimidinyl]amino]benzonitrile;

4-[[5-chloro-4-[(2,4,6-trimethylphenyl)amino]-2-pyrimidinyl]amino]benzonitrile;

4-[[5-bromo-4-(4-cyano-2,6-dimethylphenoxy)-2-pyrimidinyl]amino]benzonitrile;

4-[[4-amino-5-chloro-6-[(4-cyano-2,6-dimethylphenyl)amino]-2-pyrimidinyl]amino]benzonitrile;

4-[[5-bromo-6-[(4-cyano-2,6-dimethylphenyl)amino]-2-pyrimidinyl]amino]benzonitrile;

4-[[4-amino-5-chloro-6-(4-cyano-2,6-dimethylphenyloxy)-2-pyrimidinyl]amino]benzonitrile; and 4-[[4-amino-5-bromo-6-(4-cyano-2,6-dimethylphenyloxy)-2-pyrimidyl]amino]benzonitrile; the N-oxides, the addition salts, the quaternary amines and the stereochemically isomeric forms thereof.

In general, compounds of formula (I-a) can be prepared by reacting an intermediate of formula (II) wherein $W^1$ is a suitable leaving group such as, for example, a halogen, hydroxy, triflate, tosylate, thiomethyl, methylsulfonyl, trifluoromethylsulfonyl and the like, with an amino derivative of formula (III) optionally under solvent-free conditions or in a reaction-inert solvent such as, for example, ethanol, 1-methyl-2-pyrrolidinone, N,N-dimethylformamide, 1,4-dioxane, tetrahydrofuran, dimethyl sulfoxide, tetraline, sulfolane, acetonitrile and the like, under a reaction-inert atmosphere such as, for example, oxygen free argon or nitrogen, and optionally in the presence of an acid such as, for example, 1 N hydrochloric acid in diethyl ether or the like. This reaction can be performed at a temperature ranging between 50° C. and 250° C.

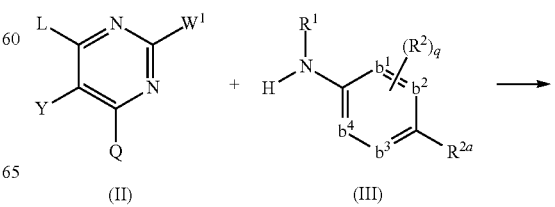

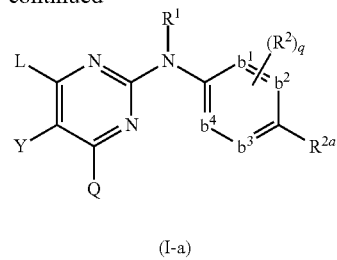

(I-a)

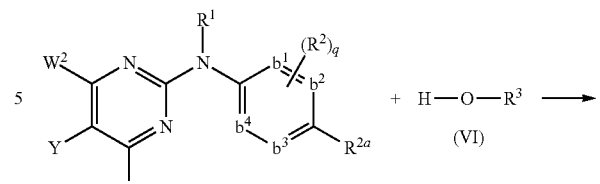

In this and the following preparations, the reaction products may be isolated from the reaction medium and, if necessary, further purified according to methodologies generally known in the art such as, for example, extraction, crystallization, distillation, trituration and chromatography.

The compounds of formula (I-a) wherein L is a radical of formula —$NR^1$—$R^3$, said compounds being represented by formula (I-a-1), can be prepared by reacting an intermediate of formula (IV) wherein $W^2$ is a suitable leaving group such as, for example, a halogen or a triflate, with an intermediate of formula (V) under solvent-free conditions or in an appropriate solvent such as, for example, ethanol, 1-methyl-2-pyrrolidinone, N,N-dimethylformamide, 1,4-dioxane, tetrahydrofuran, dimethyl sulfoxide, tetraline, sulfolane, acetonitrile and the like, under a reaction-inert atmosphere such as, for example, oxygen free argon or nitrogen, and optionally in the presence of an acid such as, for example, 1 N hydrochloric acid in diethyl ether. This reaction can be performed at a temperature ranging between 50° C. and 250° C.

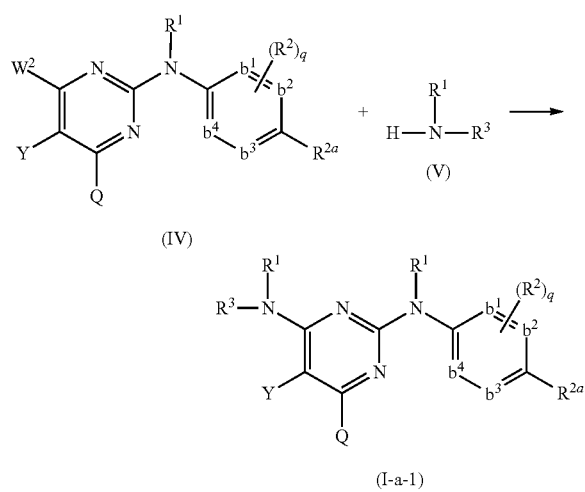

The compounds of formula (I-a) wherein L is a radical of formula —O—$R^3$, said compounds being represented by formula (I-a-2), can be prepared by reacting an intermediate of formula (IV) wherein $W^2$ is a suitable leaving group such as, for example a halogen or a triflate, with an intermediate of formula (VI) in an appropriate solvent such as, for example, 1,4-dioxane, dimethyl sulfoxide, tetraline, sulfolane and the like under a reaction-inert atmosphere such as, for example, oxygen free argon or nitrogen, and in the presence of a base such as, for example, sodium hydride, potassium hydride, sodium hydroxide or the like. This reaction can be performed at a temperature ranging between 50° C. and 250° C.

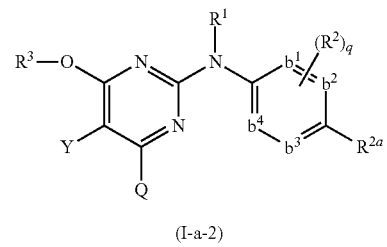

The compounds of formula (I-a) may further be prepared by converting compounds of formula (I-a) into each other according to art-known group transformation reactions.

The compounds of formula (I-a) may be converted to the corresponding N-oxide forms following art-known procedures for converting a trivalent nitrogen into its N-oxide form. Said N-oxidation reaction may generally be carried out by reacting the starting material of formula (I-a) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t.butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

For instance, the compounds of formula (I-a) wherein Q is a halogen may be converted to the corresponding compounds wherein Q is —$NR^4H$ using $NH_2R^4$ as a reagent in a reaction inert solvent such as, for example, 1,4-dioxane and the like, optionally in the presence of a suitable base such as, for example, triethylamine or N,N-diisopropylethylamine or the like. In case $R^4$ contains a hydroxy moiety, it may be convenient to perform the above reaction with a protected form of $NH_2R^4$ whereby the hydroxy moiety bears a suitable protecting group P being, for instance, a trialkylsilyl group, and subsequently removing the protective group according to art-known methodologies.

Some of the compounds of formula (I-a) and some of the intermediates in the present invention may contain an asymmetric carbon atom. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomers. Pure stereochemically isomeric forms may also be obtained from the pure stereochemically isomeric forms of the appropriate intermediates and starting materials, provided that the intervening reactions occur stereospecifically.

An alternative manner of separating the enantiomeric forms of the compounds of formula (I-a) and intermediates involves liquid chromatography, in particular liquid chromatography using a chiral stationary phase.

Some of the intermediates and starting materials are known compounds and may be commercially available or may be prepared according to art-known procedures.

Intermediates of formula (II) wherein L is —X—R³, said intermediates being represented by formula (II-1) can be prepared by reacting a pyrimidine derivative of formula (VII) wherein each W¹ is as defined previously, with HXR³ (VIII) in a reaction inert solvent such as, for example, 1,4-dioxane, 2-propanol or the like, and in the presence of a base such as, for example, triethylamine or N,N-diisopropylethylamine or the like. Different regio-specific isomers may be formed and can be separated from one another using suitable separation techniques such as, for example, chromatography.

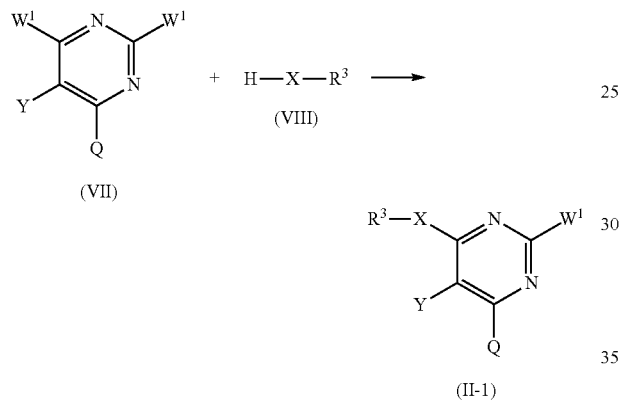

Intermediates of formula (IV) can be prepared by reacting an intermediate of formula (VII-a) wherein W² is a suitable leaving group such as, for example, a halogen, with an intermediate of formula (IX) in a suitable solvent such as, for example, 1-methyl-2-pyrrolidinone, 1,4-dioxane or the like, in the presence of an acid such as, for example, 1 N hydrochloric acid in diethyl ether. This reaction can be performed at a temperature ranging between 50° C. and 250° C.

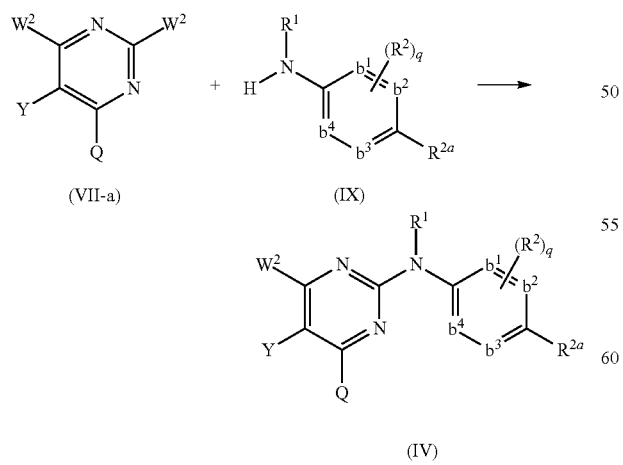

Alternatively, intermediates of formula (IV) can be prepared by reacting an intermediate of formula (X) with phosphorous oxychloride, triflic anhydride or a functional derivative thereof under a reaction-inert atmosphere such as, for example, oxygen free argon or nitrogen. This reaction can be performed at a temperature ranging between 20° C. and 150° C.

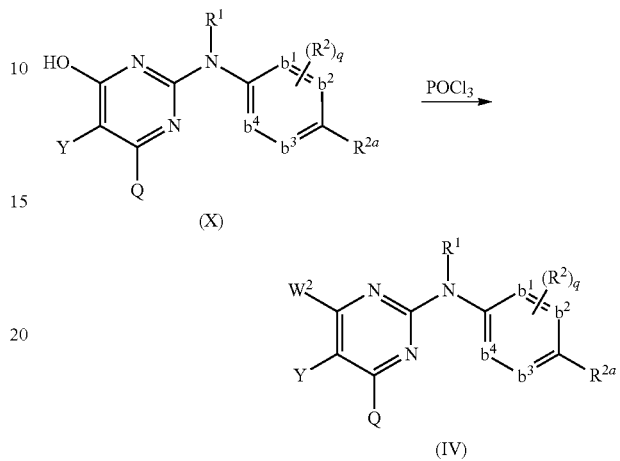

Intermediates of formula (X) can be prepared by reacting an intermediate of formula (XI) or a functional derivative thereof, with an intermediate of formula (IX). This reaction may be performed under solvent-free conditions or in an appropriate solvent such as, for example, diglyme, tetraline or the like under a reaction-inert atmosphere such as, for example, oxygen free argon or nitrogen, and optionally in the presence of a base such as, for example, sodium hydride, potassium hydride or the like. This reaction can be performed at a temperature ranging between 100° C. and 250° C.

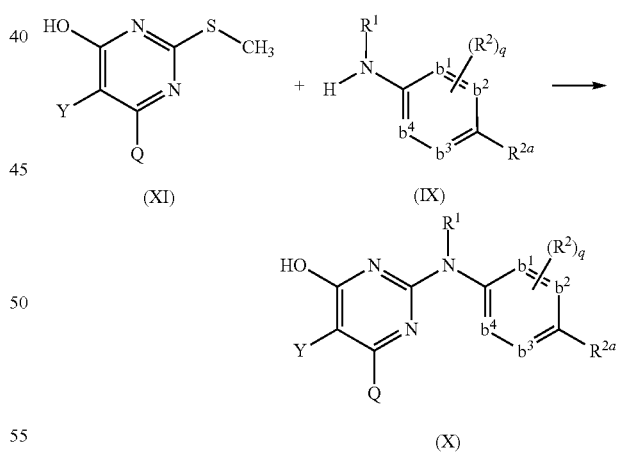

Intermediates of formula (X) can also be prepared by reacting an intermediate of formula (XII), wherein W² is a suitable leaving group and Y and Q are as defined for a compound of formula (I-a), with an intermediate of formula (XIII) in an appropriate solvent such as, for example, ethanol, or the like, and in the presence of a base such as, for example, sodium ethoxide or the like, under a reaction-inert atmosphere such as, for example, oxygen free argon or nitrogen. The reaction can be performed at a temperature ranging between 20° C. and 125° C.

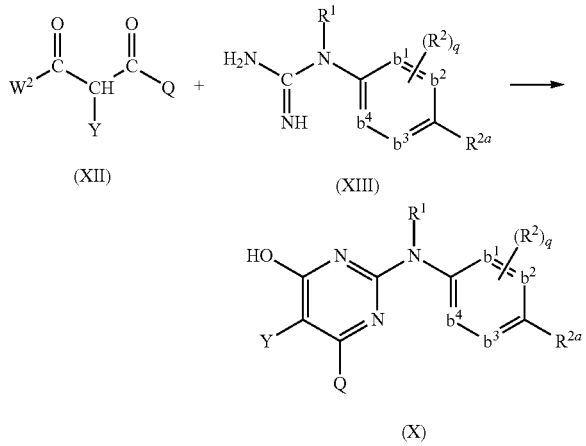

(XII) (XIII)

(X)

A convenient way of preparing an intermediate of formula (IV) wherein Y is a bromine or chloro atom, said intermediates being represented by formula (IV-1), involves the introduction of a bromine or chloro atom to an intermediate of formula (XIV), wherein $W^2$ is as previously defined, using N-bromosuccinimide or N-chlorosuccinimide in a reaction-inert solvent such as, for example, chloroform, carbon tetrachloride or the like. This reaction can be performed at a temperature ranging between 20° C. and 125° C.

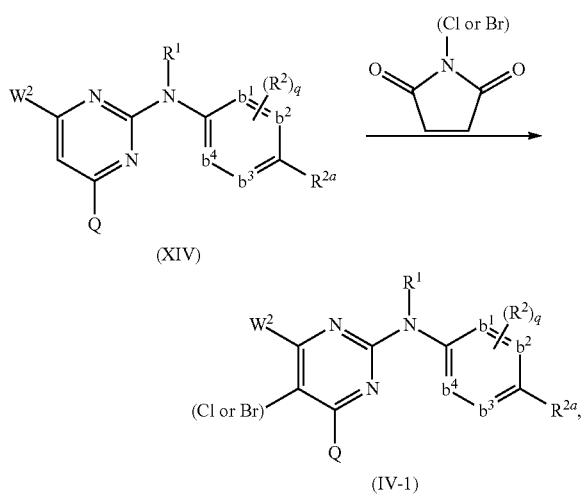

(XIV)

(IV-1)

Analogous to the conversion of compounds of formula (I-a) wherein Q is a halogen to compounds of formula (I-a) wherein Q is —NHR$^4$, the intermediates of formula (II), (IV) and (VII) can also be converted.

The compounds of formula (I-a) as prepared in the hereinabove described processes may be synthesized as a mixture of stereoisomeric forms, in particular in the form of racemic mixtures of enantiomers which can be separated from one another following art-known resolution procedures. The racemic compounds of formula (I-a) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I-a) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

It will be appreciated by those skilled in the art that in the processes described above the functional groups of intermediate compounds may need to be blocked by protecting groups.

Functional groups which it is desirable to protect include hydroxy, amino and carboxylic acid. Suitable protecting groups for hydroxy include trialkylsilyl groups (e.g. tert-butyldimethylsilyl, tert-butyldiphenylsilyl or trimethylsilyl), benzyl and tetrahydropyranyl. Suitable protecting groups for amino include tert-butyloxycarbonyl or benzyloxycarbonyl. Suitable protecting groups for carboxylic acid include $C_{1-6}$alkyl or benzyl esters.

The protection and deprotection of functional groups may take place before or after a reaction step.

The use of protecting groups is fully described in 'Protective Groups in Organic Chemistry', edited by J W F McOmie, Plenum Press (1973), and 'Protective Groups in Organic Synthesis' $2^{nd}$ edition, T W Greene & P G M Wutz, Wiley Interscience (1991).

The compounds of formula (I) and (I-a) show antiretroviral properties, in particular against Human Immunodeficiency Virus (HIV), which is the aetiological agent of Acquired Immune Deficiency Syndrome (AIDS) in humans. The HIV virus preferentially infects human T-4 cells and destroys them or changes their normal function, particularly the coordination of the immune system. As a result, an infected patient has an everdecreasing number of T-4 cells, which moreover behave abnormally. Hence, the immunological defense system is unable to combat infections and neoplasms and the HIV infected subject usually dies by opportunistic infections such as pneumonia, or by cancers. Other conditions associated with HIV infection include thrombocytopaenia, Kaposi's sarcoma and infection of the central nervous system characterized by progressive demyelination, resulting in dementia and symptoms such as, progressive dysarthria, ataxia and disorientation. HIV infection further has also been associated with peripheral neuropathy, progressive generalized lymphadenopathy (PGL) and AIDS-related complex (ARC).

The present compounds also show activity against HIV-1 strains that have acquired resistance to art-known non-nucleoside reverse transcriptase inhibitors. They also have little or no binding affinity to human α-1 acid glycoprotein.

Due to their antiretroviral properties, particularly their anti-HIV properties, especially their anti-HIV-1-activity, the compounds of formula (I) or (I-a), their N-oxides, pharmaceutically acceptable addition salts, quaternary amines and stereochemically isomeric forms thereof, are useful in the treatment of individuals infected by HIV and for the prophylaxis of these infections. In general, the compounds of the present invention may be useful in the treatment of warm-blooded animals infected with viruses whose existence is mediated by, or depends upon, the enzyme reverse transcriptase. Conditions which may be prevented or treated with the compounds of the present invention, especially conditions associated with HIV and other pathogenic retroviruses, include AIDS, AIDS-related complex (ARC), progressive generalized lymphadenopathy (PGL), as well as chronic CNS diseases caused by retroviruses, such as, for example HIV mediated dementia and multiple sclerosis.

The compounds of the present invention or any subgroup thereof may therefore be used as medicines against above-mentioned conditions. Said use as a medicine or method of treatment comprises the systemic administration to HIV-infected subjects of an amount effective to combat the conditions associated with HIV and other pathogenic retroviruses, especially HIV-1.

The compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

To aid solubility of the compounds of formula (I-a), suitable ingredients, e.g. cyclodextrins, may be included in the compositions. Appropriate cyclodextrins are α-, β-, γ-cyclodextrins or ethers and mixed ethers thereof wherein one or more of the hydroxy groups of the anhydroglucose units of the cyclodextrin are substituted with $C_{1-6}$alkyl, particularly methyl, ethyl or isopropyl, e.g. randomly methylated β-CD; hydroxy$C_{1-6}$alkyl, particularly hydroxyethyl, hydroxy-propyl or hydroxybutyl; carboxy$C_{1-6}$alkyl, particularly carboxymethyl or carboxy-ethyl; $C_{1-6}$alkylcarbonyl, particularly acetyl. Especially noteworthy as complexants and/or solubilizers are β-CD, randomly methylated β-CD, 2,6-dimethyl-β-CD, 2-hydroxyethyl-β-CD, 2-hydroxyethyl-γ-CD, 2-hydroxypropyl-γ-CD and (2-carboxymethoxy)propyl-β-CD, and in particular 2-hydroxypropyl-β-CD (2-HP-β-CD).

The term mixed ether denotes cyclodextrin derivatives wherein at least two cyclodextrin hydroxy groups are etherified with different groups such as, for example, hydroxypropyl and hydroxyethyl.

The average molar substitution (M.S.) is used as a measure of the average number of moles of alkoxy units per mole of anhydroglucose. The average substitution degree (D.S.) refers to the average number of substituted hydroxyls per anhydroglucose unit. The M.S. and D.S. value can be determined by various analytical techniques such as nuclear magnetic resonance (NMR), mass spectrometry (MS) and infrared spectroscopy (IR). Depending on the technique used, slightly different values may be obtained for one given cyclodextrin derivative. Preferably, as measured by mass spectrometry, the M.S. ranges from 0.125 to 10 and the D.S. ranges from 0.125 to 3.

Other suitable compositions for oral or rectal administration comprise particles obtainable by melt-extruding a mixture comprising a compound of formula (I-a) and an appropriate water-soluble polymer and subsequently milling said melt-extruded mixture. Said particles can then be formulated by conventional techniques into pharmaceutical dosage forms such as tablets and capsules.

Said particles consist of a solid dispersion comprising a compound of formula (I-a) and one or more pharmaceutically acceptable water-soluble polymers. The preferred technique for preparing solid dispersions is the melt-extrusion process comprising the following steps:
 a) mixing a compound of formula (I-a) and an appropriate water-soluble polymer,
 b) optionally blending additives with the thus obtained mixture,
 c) heating the thus obtained blend until one obtains a homogenous melt,
 d) forcing the thus obtained melt through one or more nozzles; and
 e) cooling the melt till it solidifies.

The solid dispersion product is milled or ground to particles having a particle size of less than 1500 μm, preferably less than 400 μm, more preferably less than 250 μm and most preferably less than 125 μm.

The water-soluble polymers in the particles are polymers that have an apparent viscosity, when dissolved at 20° C. in an aqueous solution at 2% (w/v), of 1 to 5000 mPa·s, more preferably of 1 to 700 mPa·s, and most preferred of 1 to 100 mPa·s. For example, suitable water-soluble polymers include alkylcelluloses, hydroxyalkylcelluloses, hydroxyalkyl alkylcelluloses, carboxyalkylcelluloses, alkali metal salts of carboxyalkylcelluloses, carboxyalkylalkylcelluloses, carboxyalkylcellulose esters, starches, pectines, chitin derivates, polysaccharides, polyacrylic acids and the salts thereof, polymethacrylic acids and the salts and esters thereof, methacrylate copolymers, polyvinylalcohol, polyalkylene oxides and copolymers of ethylene oxide and propylene oxide. Preferred water-soluble polymers are Eudragit E® (Röhm GmbH, Germany) and hydroxypropyl methylcelluloses.

Also one or more cyclodextrins can be used as water soluble polymer in the preparation of the above-mentioned particles as is disclosed in WO 97/18839. Said cyclodextrins include the pharmaceutically acceptable unsubstituted and substituted cyclodextrins known in the art, more particularly α, β or γ cyclodextrins or the pharmaceutically acceptable derivatives thereof.

Substituted cyclodextrins which can be used include polyethers described in U.S. Pat. No. 3,459,731. Further substituted cyclodextrins are ethers wherein the hydrogen of one or more cyclodextrin hydroxy groups is replaced by $C_{1-6}$alkyl, hydroxy$C_{1-6}$alkyl, carboxy-$C_{1-6}$alkyl or $C_{1-6}$alkyloxycarbonyl$C_{1-6}$alkyl or mixed ethers thereof. In particular such substituted cyclodextrins are ethers wherein the hydrogen of one or more cyclodextrin hydroxy groups is replaced by $C_{1-3}$alkyl, hydroxy$C_{2-4}$alkyl or carboxy$C_{1-2}$alkyl or more in particular by methyl, ethyl, hydroxyethyl, hydroxypropyl, hydroxybutyl, carboxy-methyl or carboxyethyl.

Of particular utility are the β-cyclodextrin ethers, e.g. dimethyl-β-cyclodextrin as described in Drugs of the Future, Vol. 9, No. 8, p. 577-578 by M. Nogradi (1984) and polyethers, e.g. hydroxypropyl β-cyclodextrin and hydroxyethyl β-cyclodextrin, being examples. Such an alkyl ether may be a methyl ether with a degree of substitution of about 0.125 to 3, e.g. about 0.3 to 2. Such a hydroxypropyl cyclodextrin may for example be formed from the reaction between β-cyclodextrin an propylene oxide and may have a MS value of about 0.125 to 10, e.g. about 0.3 to 3.

A more novel type of substituted cyclodextrins is sulfobutylcyclodextrines.

The ratio of the compound of formula (I-a) over cyclodextrin may vary widely. For example ratios of 1/100 to 100/1 may be applied. Interesting ratios of the compound of formula (I-a) over cyclodextrin range from about 1/10 to 10/1. More interesting ratios range from about 1/5 to 5/1.

It may further be convenient to formulate the compounds of formula (I-a) in the form of nanoparticles which have a surface modifier adsorbed on the surface thereof in an amount sufficient to maintain an effective average particle size of less than 1000 nm. Useful surface modifiers are believed to include those which physically adhere to the surface of the compound of formula (I-a) but do not chemically bond to said compound.

Suitable surface modifiers can preferably be selected from known organic and inorganic pharmaceutical excipients. Such excipients include various polymers, low molecular weight oligomers, natural products and surfactants. Preferred surface modifiers include nonionic and anionic surfactants.

Yet another interesting way of formulating the compounds of formula (I-a) involves a pharmaceutical composition whereby the compounds of formula (I-a) are incorporated in hydrophilic polymers and applying this mixture as a coat film over many small beads, thus yielding a composition which can conveniently be manufactured and which is suitable for preparing pharmaceutical dosage forms for oral administration.

Said beads comprise a central, rounded or spherical core, a coating film of a hydrophilic polymer and a compound of formula (I-a) and a seal-coating polymer layer.

Materials suitable for use as cores in the beads are manifold, provided that said materials are pharmaceutically acceptable and have appropriate dimensions and firmness. Examples of such materials are polymers, inorganic substances, organic substances, and saccharides and derivatives thereof.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Those of skill in the treatment of HIV-infection could determine the effective daily amount from the test results presented here. In general it is contemplated that an effective daily amount would be from 0.01 mg/kg to 50 mg/kg body weight, more preferably from 0.1 mg/kg to 10 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) or (I-a) used, the particular condition being treated, the severity of the condition being treated, the age, weight and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention. The effective daily amount ranges mentioned hereinabove are therefore only guidelines and are not intended to limit the scope or use of the invention to any extent.

Also, the combination of an antiretroviral compound and a compound of formula (I) or (I-a) can be used as a medicine. Thus, the present invention also relates to a product containing (a) a compound of formula (I) or (I-a), and (b) another antiretroviral compound, as a combined preparation for simultaneous, separate or sequential use in anti-HIV treatment. The different drugs may be combined in a single preparation together with pharmaceutically acceptable carriers. Said other antiretroviral compounds may be known antiretroviral compounds such as nucleoside reverse transcriptase inhibitors, e.g. zidovudine (3'-azido-3'-deoxythymidine, AZT), didanosine (dideoxy inosine; ddI), zalcitabine (dideoxycytidine, ddC) or lamivudine (3'-thia-2'-3'-dideoxycytidine, 3TC) and the like; non-nucleoside reverse transcriptase inhibitors such as suramine, pentamidine, thymopentin, castanospermine, efavirenz, dextran (dextran sulfate), foscarnet-sodium (trisodium phosphono formate), nevirapine (11-cyclopropyl-5,11-dihydro-4-methyl-6H-dipyrido[3,2-b: 2',3'-e][1,4]diazepin-6-one), tacrine (tetrahydroaminoacridine) and the like; compounds of the TIBO (tetrahydro-imidazo[4,5,1-jk][1,4]-benzodiazepine-2(1H)-one and thione)-type e.g. (S)-8-chloro-4,5,6,7-tetrahydro-5-methyl-6-(3-methyl-2-butenyl)imidazo-[4,5,1-jk][1,4]benzodiazepine-2 (1H)-thione; compounds of the α-APA (α-anilino phenyl acetamide) type e.g. α-[(2-nitro-phenyl)amino]-2,6-dichlorobenzene-acetamide and the like; TAT-inhibitors, e.g. RO-5-3335 and the like; protease inhibitors e.g. indinavir, ritanovir, saquinovir, ABT-378 and the like; or immunomodulating agents, e.g. levamisole and the like. The compound of formula (I) or (I-a) can also be combined with another compound of formula (I) or (I-a).

The following examples are intended to illustrate the present invention.

EXPERIMENTAL PART

A. Preparation of the Intermediate Compounds

Example A1

Reaction under argon atmosphere. A solution of 2,4,6-trimethylbenzenamine (0.00461 mol) in 1,4-dioxane (5 ml)

was added to a solution of 5-bromo-2,4-dichloropyrimidine (0.00439 mol) in 1,4-dioxane (5 ml). N,N-bis(1-methylethyl) ethanamine (0.00548 mol) was added. The reaction mixture was stirred and refluxed for 20 hours. The solvent was evaporated. The residue was dissolved in ethyl acetate, washed with a saturated aqueous sodium bicarbonate solution, water and brine, dried with sodium sulfate, filtered, and the solvent was evaporated. The residue was purified by column chromatography over silica gel (eluent: 1:5, 1:2 and 1:1 $CH_2Cl_2$:hexane). Two pure fraction groups were collected and their solvent was evaporated, yielding 0.35 g (24%) of 5-bromo-4-chloro-N-(2,4,6-trimethylphenyl)-2-pyrimidinamine (interm. 1) and 0.93 g (65%) of 5-bromo-2-chloro-N-(2,4,6-trimethylphenyl)-4-pyrimidinamine (interim 2).

Example A2 a) 4-Hydroxy-5-chloro-2-methylthiopyrimidine (0.0156 mol) and 4-aminobenzonitrile (0.078-mol) were combined as a melt and stirred at 180-200° C. for 6 hours. The reaction mixture was cooled, and triturated sequentially with boiling $CH_2Cl_2$ and $CH_3CN$ to obtain 95% pure compound, which was dried, yielding 1.27 g (33%) of 4-[(5-chloro-4-hydroxy-2-pyrimidinyl)amino]benzonitrile (interm. 3; mp. >300° C.).

b) $POCl_3$ (10 ml) was added to intermediate (3) (0.0028 mol). The flask was equipped with a condenser and heated to 80° C. for 35 minutes. The material was quenched on ice and allowed and the resulting precipitate was collected and washed with water (50 ml). The sample was dried. A fraction thereof was further purified by column chromatography. The pure fractions were collected and the solvent was evaporated, yielding 4-[(4,5-dichloro-2-pyrimidinyl)amino]benzonitrile (interim 4).

c) The mixture of intermediate (4) (0.0132 mol) in tetrahydrofuran (75 ml) and $CH_2Cl_2$ (10 ml) was stirred for 15 min. HCl in diethyl ether (0.0145 mop was added slowly, and the mixture was stirred for 5 minutes. The solvent was removed under reduced pressure, yielding 3.98 g of 4-[(4,5-dichloro-2-pyrimidinyl)amino]benzonitrile monohydrochloride (interim 5).

Example A3 a) 2,4,5,6-tetrachloropyrimidine (0.0134 mol), 1,4-dioxane (30 ml), 2,4,6-trimethyl aniline (0.0134 mol), and N,N-bis(1-methylethyl)ethanamine (0.0136 mol) were added to a flask under argon and stirred at 55° C. for 16 hours. The solvent was evaporated, and the residue was dissolved in $CH_2Cl_2$, then purified by column chromatography over silica gel (eluent: $CH_2Cl_2$/hexane ¼, and ½). The desired fractions were collected and their solvent was evaporated, yielding 0.15 g 4,5,6-trichloro-N-(2,4,6-trimethylphenyl)-2-pyrimidinamine (interm. 6) and 3.15 g 2,5,6-trichloro-N-(2,4,6-trimethylphenyl)-4-pyrimidinamine (interm. 7).

b) A mixture of intermediate 7 (0.00474 mol) in $NH_3$, (2.0 M in 2-propanol; 20 ml) was heated in a pressure vessel at 75-80° C. for 40 hours. The temperature was increased to 110-115° C. The solvent was evaporated to produce 1.85 g of residue. The sample was heated with $NH_3$, (0.5 M in 1,4-dioxane; 20 ml) at 125° C. for 18 hours. The solvent was evaporated, yielding 1.7 g of a mixture of two isomers, i.e. 2,5-dichloro-N4-(2,4,6-trimethylphenyl)-4,6-pyrimidinediamine (interm. 8) and 5,6-dichloro-N4-(2,4,6-trimethylphenyl)-2,4-pyrimidinediamine (interm. 9).

Example A4 a) A mixture of 4-[(1,4-dihydro-4-oxo-2-pyrimidinyl) amino]benzonitrile, (0.12 mol) in $POCl_3$ (90 ml) was stirred and refluxed under Argon for 20 minutes. The reaction mixture was slowly poured onto 750 ml ice/water, and the solid was separated by filtration. The solid was suspended in 500 ml water, and the pH of the suspension was adjusted to neutral by adding a 20% NaOH solution. The solid was again separated by filtration, suspended in 200 ml 2-propanone, and 1000 ml $CH_2Cl_2$ was added. The mixture was heated until all solid had dissolved. After cooling to room temperature, the aqueous layer was separated, and the organic layer was dried. During removal of the drying agent by filtration, a white solid formed in the filtrate. Further cooling of the filtrate in the freezer, followed by filtration, yielded 21.38 g (77.2%) of 4-[(4-chloro-2-pyrimidinyl)amino]benzonitrile (interm. 10).

b) Intermediate (10) (0.005 mol), 1-bromo-2,5-pyrrolidinedione (0.006 mol) and trichloromethane (10 ml) were combined in a sealed tube and heated at 100° C. overnight. The reaction mixture was allowed to cool to room temperature. Silica gel (2 g) was added, and the solvent was evaporated. The residue was purified by flash column chromatography over silica gel (eluent: $CH_2Cl_2$/hexanes 9/1). The pure fractions were collected and the solvent was evaporated, yielding 1.31 g (84.5%) of 4-[(5-bromo-4-chloro-2-pyrimidinyl)amino]benzonitrile (interm. 11).

Example A5

To a flask under Argon was added 4-amino-2,5,6-trichloropyrimidine (0.08564 mol), 4-amino-benzonitrile (0.1071 mol), 1-methyl-2-pyrrolidinone (17 ml) and HCl in diethyl-ether (1M; 85.6 ml). The mixture was placed in an oil bath at 130° C. under a stream of nitrogen until the ether was gone. An additional 10 ml of 1-methyl-2-pyrrolidinone was added. The mixture was heated at 145° C. for 16 hours under argon. 1,4-Dioxane was added. The mixture was refluxed, cooled, then filtered. The filtrate was evaporated. The residue was dissolved in $CH_2Cl_2$, washed with 1 N NaOH, then filtered. The solid was dissolved in 2-propanone, evaporated onto silica gel, and chromatographed using 1-3% 2-propanone in hexane as eluent. The pure fractions were collected and the solvent was evaporated, yielding 1.63 g (6.8%) of 4-[(4-amino-5,6-dichloro-2-pyrimidinyl)amino]benzonitrile (interm. 12).

B. Preparation of the Final Compound

Example B1 a) To a flask under argon containing intermediate (1) (0.00107 mol) was added ether. To this homogeneous solution was added HCl/diethylether (1M; 0.00109 mol). The solvent was evaporated and 1,4-dioxane (35 ml) and 4-aminobenzonitrile (0.00322 mol) were added. The reaction mixture was stirred and refluxed for 4 days. The solvent was evaporated. The residue was dissolved in $CH_2Cl_2$, washed with a saturated sodium bicarbonate solution, dried, filtered and the solvent was evaporated to give 0.79 g of amber oil. The oil was purified by reverse phase HPLC. The desired fractions were collected and the solvent was evaporated, yielding residues 1 and 2.

Residue 1 was purified by column chromatography over silica gel (eluent: 0 and 2% $CH_3OH$:$CH_2Cl_2$). The pure fractions were collected and the solvent was evaporated, yielding 0.0079 g (2.0%) of 4-[[5-chloro-2-[(2,4,6-trimethylphenyl) amino]-4-pyrimidinyl]amino]benzonitrile (compound 1).

Residue 2 was purified by column chromatography over silica gel (eluent: 0 and 2% $CH_3OH$:$CH_2Cl_2$). The pure fractions were collected and the solvent was evaporated, yielding 0.0044 g (1.0%) of 4-[[5-bromo-2-[(2,4,6-trimethylphenyl)amino]-4-pyrimidinyl]amino]benzonitrile (compound 2).

b) To a flask containing intermediate 2 (0.00285 mop was added ether. To this homogeneous solution was added HCl in diethyl ether (1M; 0.00855 mol). The solvent was evaporated and 1,4-dioxane (20 ml) was added. Finally, 4-aminobenzonitrile (0.00291 mol) and 1,4-dioxane (15 ml) were added and the reaction mixture was stirred and refluxed for seven days. The solvent was evaporated, the residue dissolved in $CH_2Cl_2$, washed with 1 M NaOH, and the solvent evaporated. The residue was dissolved in $CH_2Cl_2$ (10 ml) and the precipitate was filtered off and dried, yielding 0.15 g (13%) of 4-[[5-bromo-4-[(2,4,6-trimethylphenyl)amino]-2-pyrimidinyl]amino]benzonitrile (comp. 3).

Example B2 a) A 3:1 mixture of intermediate (8) and intermediate (9) [as prepared in example A3b] and 4-aminobenzonitrile (0.01422 mol) was heated in a pressure vessel at 180° C. for 5 hours. The sample was partitioned between $CH_2Cl_2$ and diluted $NaHCO_3$, dried over $K_2CO_3$, filtered, and evaporated. $CH_3CN$ was stirred in, the resulting precipitate removed by filtration. The filtrate was further purified by reverse phase HPLC. The pure fractions were collected and the solvent was evaporated, yielding 0.17 g of 4-[[4-amino-5-chloro-6-[(2,4,6-trimethylphenyl)amino]-2-pyrimidinyl]amino]benzonitrile trifluoroacetate (1:1) (comp. 4).

Example B3

HCl in diethylether (1M; 0.0045 mol) was added to a suspension of intermediate (4) (0.003 mol) in 1,4-dioxane (5 ml), stirred under argon in a sealable tube. The mixture was warmed to evaporate the diethylether, and 2,4,6-trimethylbenzenamine (0.009 mol) was added. The tube was sealed, and the reaction mixture was heated to 150° C. for 12 hours. The reaction mixture was allowed to cool to room temperature. Sequentially, silica gel (2.2 g) and $CH_3OH$ (50 ml) were added. After evaporating the solvent, the residue was purified by flash chromatography (eluent gradient: $CH_2Cl_2$:$CH_3OH$:$NH_4OH$ 99.5:0.45:0.05 up to 99:0.9:0.1). The pure fractions were collected and the solvent was evaporated. The residue was dried, yielding 0.80 g (73.4%) of 4-[[5-chloro-4-[(2,4,6-trimethylphenyl)amino]-2-pyrimidinyl]amino]benzonitrile (comp. 5).

Example B4

A mixture of intermediate (5) (0.0025 mol) and 2,6-dibromo-4-methylbenzenamine (0.0075 mol) in 1,3-dioxane (5.0 ml) in a sealed tube under argon was heated and stirred at 160° C. for 16 hours. The reaction mixture was concentrated by rotary evaporation onto silica gel (2.0 g). The material was purified by flash chromatography (eluent 1:1 hexanes:$CH_2Cl_2$; neat $CH_2Cl_2$; 0.5%, 1% (10% $NH_4OH$ in $CH_3OH$) in $CH_2Cl_2$) for 90% purity. Recrystallization afforded 0.15 g (12.2%) of 4-[[5-chloro-4-[(2,6-dibromo-4-methylphenyl)amino]-2-pyrimidinyl]amino]benzonitrile (comp. 10; 95% purity).

Example B5

NaH (0.0075 mol; 60% suspension in oil) was added to a suspension of 2,4,6-trimethylphenol (0.0075 mol) in 1,4-dioxane (5 ml) in a sealable tube under argon. The mixture was stirred for 15 minutes, and intermediate (4) (0.0025 mol) was added. The tube was sealed, and the reaction mixture was heated to 150° C. for 15 hours. The reaction was allowed to cool to room temperature. After silica gel (2.0 g) was added, the solvent was evaporated. The residue was purified by flash column chromatography over silica gel (eluent gradient: $CH_2Cl_2$:hexanes 9:1 up to 100:0; then $CH_2Cl_2$:$CH_3OH$:$NH_4OH$ 100:0:0 up to 97:2.7:0.3). The pure fractions were collected and the solvent was evaporated. The residue was dried, yielding 0.73 g of (80.2%) 4-[[5-chloro-4-(2,4,6-trimethylphenoxy)-2-pyrimidinyl]amino]benzonitrile (comp. 6).

Example B6 a) NaH, 60% suspension in oil (0.003 mol) and 1-methyl-2-pyrrolidinone (3 ml) were added to a suspension of 4-hydroxy-3,5-dimethylbenzonitrile (0.003 mol) in 1,4-dioxane (3 ml) in a sealable tube under argon. After the $H_2$ had evolved, intermediate (11) (0.001 mol) was added. The tube was sealed and the reaction mixture was heated to 160° C. for 16 hours. The mixture was cooled to room temperature, transferred to a beaker and diluted with methanol (20 ml). Water (200 ml) was added dropwise. The aqueous mixture was extracted with $CH_2Cl_2$/$CH_3OH$ 90/10 (3×300 ml). The organic layer was separated, dried, filtered and adsorbed onto silica gel (1 g). The solvent was evaporated and the residue was purified by flash column chromatography over silica gel (eluent: $CH_2Cl_2$/$CH_3OH$/$NH_4OH$ from 100/0/0 to 98/1.8/0.2). The desired fractions were collected and the solvent was evaporated. The residue was triturated with hot $CH_3CN$, filtered off, then dried, yielding 0.20 g (47.6%) of 4-[[5-bromo-4-(4-cyano-2,6-dimethylphenoxy)-2-pyrimidinyl]amino]benzonitrile (comp. 17).

b) n-Butyllithium (0.010 mol) was added to a solution of N-(1-methylethyl)-2-propanamine (0.010 mol) in tetrahydrofuran (250 ml), stirred at 0° C. After stirring cold for 30 min, compound (17) (0.005 mol) was added. The resulting mixture was stirred cold for 15 min at which point ethyl 2-bromoethanoate (0.015 mol) was added and the temperature was allowed to rise to room temperature and the reaction mixture was stirred for 16 hours which drove the reaction to 50% completion. Quenched with 0.5 ml $H_2O$, the sample was concentrated by rotary evaporation onto silica gel, and purified by flash chromatography (Biotage Flash 40M, eluting with 0, 0.5, 1% (10% $NH_4OH$ in $CH_3OH$) in $CH_2Cl_2$) to give a white solid which was 1:1 starting material A:product. Preparatory HPLC purification eluting into tubes containing 1 mmol $NaHCO_3$ effected final purification. Lyophilized material was taken up in water/$CH_2Cl_2$ (1:1 (50 ml total)) and separated. The aqueous phase was extracted 2 more times with 25 ml $CH_2Cl_2$. The organic layers were combined and dried over sodium sulfate, filtered and rotary evaporated to white solid dried in vacuo at 65° C. 18 hours. Yield: 0.33 g of

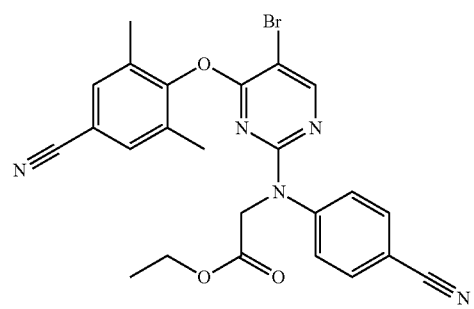 [SMILES: CCOC(=O)CN(c1ccc(C#N)cc1)c1ncc(Br)c(Oc2c(C)cc(C#N)cc2C)n1]

(13%, white solid); mp. 185-190° C. (comp. 59).

c) Reaction under Ar flow. NaH 60% (0.00600 mol) was stirred in tetrahydrofuran (20 ml). Compound (17) (0.00476 mol) was added and the mixture was stirred for 15 min. Chloromethyl-2,2-dimethylpropanoate (0.00600 mol) was added and the reaction mixture was stirred for 16 hours at room temperature, then stirred and refluxed for 4.5 hours, then cooled. Tetrahydrofuran (20 ml) was added. NaH 60% (0.00600 mol) and chloromethyl-2,2-dimethylpropanoate (0.00600 mol) were added and the resulting reaction mixture was stirred for 24 hours. The solvent was evaporated. The residue was dissolved in CH$_2$Cl$_2$, washed with water, and the solvent was evaporated. The residue was purified by column chromatography over silica gel (eluent: CH$_2$Cl$_2$/CH$_3$OH 100/0 and 99.5/0.5). The desired fractions were collected and the solvent was evaporated. The residue was purified on the Gilson. This fraction was crystallized from 2-propanol, filtered off and dried. Yield: 0.60 g of

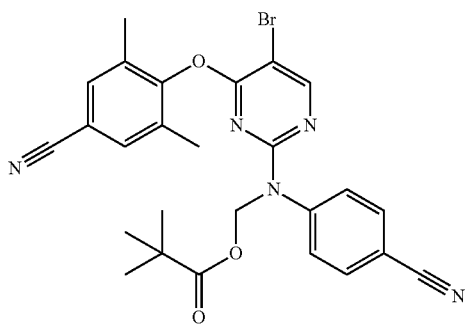 [SMILES: Cc1cc(C#N)cc(C)c1Oc1nc(N(COC(=O)C(C)(C)C)c2ccc(C#N)cc2)ncc1Br]

(23.6%, white solid) (comp. 60).

d) A suspension of compound (17) (0.0020 mol) in tetrahydrofuran (40 ml) was treated with 0.24 g of NaH in one portion. The effervescent mixture was stirred for 2 hours to afford a bright yellow suspension. A solution of 2,2'-oxybisacetyl chloride (0.020 mol) in tetrahydrofuran (10 ml) was prepared and cooled in an ice bath. Via cannula, the resultant A/B suspension was transferred to the cold solution of 2,2'-oxybisacetyl chloride dropwise over 10 minutes. The mixture was warmed to room temperature and stirred for 3 days. Another 0.24 g of NaH was added and after 2 days the reaction was cooled in an ice bath and treated with a mixture of methanol (0.150 mol) and N,N-diethylethanamine (0.150 mol) dropwise over 30 minutes. The reaction mixture was warmed to room temperature and after 16 hours poured into ether and extracted with saturated NaHCO$_3$. The aqueous fraction was extracted 2× with ether and the combined ether extracts were backwashed 3× with water and dried over MgSO$_4$. Concentration afforded 2.91 g of an oily residue that was subjected to reverse phase prep HPLC. Lyophilization of the appropriate fractions provided 0.16 g of the

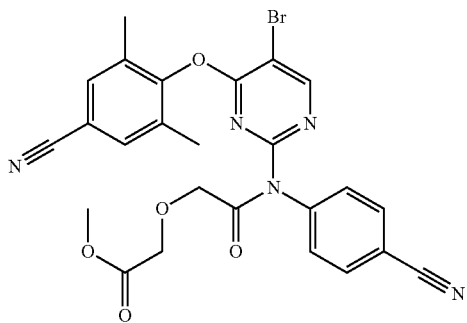 [SMILES: COC(=O)COCC(=O)N(c1ccc(C#N)cc1)c1ncc(Br)c(Oc2c(C)cc(C#N)cc2C)n1]

sample as a beige powder (14.5% purified yield) (comp. 61).

Example B7

To a pressure vessel under argon was added intermediate 12 (0.00286 mol), 4-cyano-2,6-dimethylaniline (0.00571 mol), 1M HCl in diethyl ether (0.00140 mol) and 1,4-dioxane (8 ml). The reaction mixture was heated in an oil bath under a stream of nitrogen until all the solvents had evaporated. 1-methyl-2-pyrrolidinone (3 ml) was added, and the reaction mixture heated at 220-240° C. for 3 hours. Heating was continued at 210-220° C. for 6 hours. The residue was dissolved in 1,4-dioxane, evaporated, partitioned between CH$_2$Cl$_2$ and 1 N NaOH, filtered, dried organic layers with potassium carbonate and evaporated. The desired compound was isolated and purified by preparative reverse phase chromatography. The pure fractions were collected and the solvent was evaporated, yielding 0.0165 g (1.1% after lyophilization) of 4-[[4-amino-5-chloro-6-[(4-cyano-2,6-dimethylphenyl)amino]-2-pyrimidinyl]amino]benzonitrile trifluoroacetate (1:1) (comp. 19).

Example B8

A mixture of intermediate (11) (0.0011 mol), 2,6-dimethyl-4-(2-propyl)benzenamine (0.0011 mol), N,N,N',N'-tetramethyl-1,8-naphthalenediamine (0.0022 mol) and 1 M HCl in ether (2.3 ml) (0.0023 mol) in 1,4-dioxane (25 ml) was stirred and heated to 95° C. for 16 hours. Solvent was removed by rotary evaporation and the residue was purified by reverse phase preparatory HPLC. The combined fractions containing the desired material were lyophilized to yield 0.23 g of

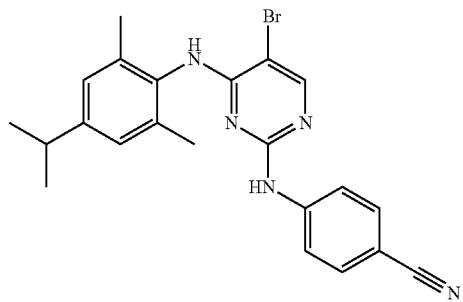 [SMILES: Cc1cc(C(C)C)cc(C)c1Nc1nc(Nc2ccc(C#N)cc2)ncc1Br]

(48%); mp. 198-201° C. (comp. 40)

Example B9

N,N-di(methylethyl)ethanamine (0.0024 mol) was added to 4-amino-2,5-dimethyl-3,4-benzonitrile (0.00219 mol) and 4-[[(5-bromo-4,6-dichloro)-2-pyrimidinyl]amino]benzonitrile (0.00218 mol). The reaction vial was sealed and heated to 155-160° C. with stirring for 1.5 days. The sample was cooled to room temperature. The sample was treated with flash column chromatography over silica gel (eluent: CH$_2$Cl$_2$). Purification was completed through preparative HPLC to yield 0.05 g of 4-[[5-bromo-4-chloro-6-[(4-cyano-2,6-dimethylphenyl)amino]-2-pyrimidinyl]amino]benzonitrile (5.0%); mp. 259-260° C. (comp. 42).

Example B10

Sequentially 2,4,6-trimethylbenzenamine (0.0022 mol) and N,N-di(methylethyl)ethanamine (0.0024 mol) were added to a solution of and 4-[[(5-bromo-4,6-dichloro)-2-pyrimidinyl]amino]benzonitrile (0.00218 mol) in 1,4-dioxane (10 ml). The tube was sealed and the suspension was heated to 120-130° C. in an oil bath while stirring for 90 hours. The mixture was cooled to room temperature. More N,N-di(methylethyl)ethanamine (15 ml) was added, and the sample was reheated to 120-130° C. for 64 hours. The reaction was heated at 150° C. for 6 days. The sample was cooled to room temperature. The sample was diluted with ethylacetate and extracted with cold 1M NaOH. The aqueous phase was backwashed with ethylacetate. The combined organic phases were dried and concentrated. Flash column chromatography over silica gel (eluent: CH$_2$Cl$_2$). The sample was further purified by preparatory HPLC to yield 0.53 g of 4-[[5-bromo-4-chloro-6-[(2,4,6-trimethylphenyl)amino]-2-pyrimidinyl]amino]benzonitrile (54.9%); mp. 220-221° C. (comp. 41).

Example B11

A mixture of 4-aminobenzonitrile (0.0043 mol) and

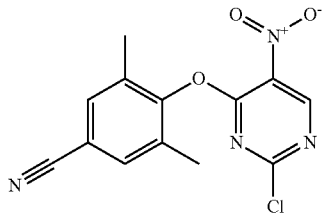 [SMILES: Cc1cc(C#N)cc(C)c1Oc1nc(Cl)ncc1[N+](=O)[O-]]

(0.0021 mol) in 1,4-dioxane (30 ml) was stirred at 100° C. for 16 hours. The solvent was removed by rotary evaporation. The solid residue was triturated and the residue was dried in vacuo at 40° C. for 16 hours, yielding 0.452 g of

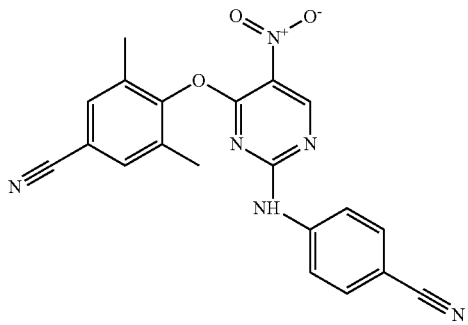 [SMILES: Cc1cc(C#N)cc(C)c1Oc1nc(Nc2ccc(C#N)cc2)ncc1[N+](=O)[O-]]

(55%); mp. >300° C. (comp. 43).

Example B12

To a pressure vessel was added

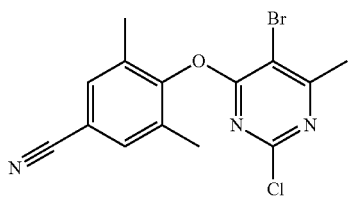 [SMILES: Cc1cc(C#N)cc(C)c1Oc1nc(Cl)nc(C)c1Br]

(0.00567 mol), 4-aminobenzonitrile (0.01163 mol) and 1-methyl-2-pyrrolidinone (20 ml). The reaction mixture was heated at 140° C. for 16 hours. The reaction mixture was cooled to room temperature and acetonitrile and water were added. The resulting precipitate was filtered, and the solid recrystallized with acetonitrile to give 1.27 g of 4-[[5-bromo-4-(4-cyano-2,6-dimethylphenoxy)-6-methyl-2-pyrimidinyl]amino]benzonitrile (52); mp. 260-262° C. (comp. 44).

Example B13

Intermediate (11) (0.001 mol) and 2,6-dimethyl-4-aminobenzonitrile (0.00473 mol) were combined and heated to 150° C. while stirring for 16 hours. The sample was dissolved in CH$_3$OH and evaporated onto silica gel (1 g) and eluted with 1:1 hexanes:CH$_2$Cl$_2$, 4:1 CH$_2$Cl$_2$:hexanes, and neat CH$_2$Cl$_2$ (2 L). The desired fractions were evaporated and the residue was dried in vacuo for 16 hours at 45° C. The thus obtained was transferred to a 4 ml vial in CH$_2$Cl$_2$ and the solvent was evaporated, yielding 0.120 g of 4-[[5-bromo-6-[(4-cyano-2,6-dimethylphenyl)amino]-2-pyrimidinyl]amino]benzonitrile (28.6%); mp. 277-280° C. (comp. 45).

Example B14

4-[[5-bromo-4-(4-cyano-2,6-dimethylphenoxy)-6-chloro-2-pyrimidinyl]amino]benzonitrile (0.00250 mol) and NH$_3$/1,4-dioxane 0.5M (0.015 mol) were heated in a pressure vessel at 150° C. for 4 days. The sample was allowed to sit at ambient conditions for 2 days. Water was added slowly to the mixture until a precipitate formed. The mixture was stirred for 2 hours and filtered. The solid was recrystallized from CH$_3$CN to obtain 0.58 g (fraction 1). The filtrate was evaporated (fraction 2). Both fractions were combined and purified by column chromatography, eluting with CH$_2$Cl$_2$. The resulting residue of the desired fraction was recrystallized from CH$_3$CN to yield 0.44 g of 4-[[4-amino-5-bromo-6-(4-cyano-2,6-dimethylphenyloxy)-2-pyrimidinyl]amino]benzonitrile (40.5%). The sample was dried at 80° C. for 16 hours at 0.2 mm Hg (comp. 46).

Example B15

4-[[5-bromo-4-(4-cyano-2,6-dimethylphenoxy)-6-chloro-2-pyrimidinyl]amino]benzonitrile (0.000660 mol), tetrahydrofuran (1 ml), and 1-pyrrolidineethanamine (0.00198 mol) were added to a pressure vessel. The mixture was heated at 75° C. for 16 hours. CH$_2$Cl$_2$ was added, and the mixture was washed with water, dried, filtered and the filtrate was evaporated. Purification using flash column chromatography eluting with 1:9 methanol:methylene chloride produced a solid which was redissolved in CH$_3$CN. HCl/diethylether 1.0M (0.48 ml) was added, and the mixture was cooled in ice. Filtration yielded 0.19 g of 4-[[5-bromo-4-(4-cyano-2,6-dimethylphenoxy)-6-[(1-pyrrolidinyl)ethylamino]-2-pyrimidinyl]amino]benzonitrile hydrochloride (1:1) (50.6%); mp. 208-210° C. (comp. 47).

Example B16

To a pressure vessel was added 4-[[5-bromo-4-(4-cyano-2,6-dimethylphenoxy)-6-chloro-2-pyrimidinyl]amino]benzonitrile (0.00064 mol), tetrahydrofuran (3 ml), O-methylhydroxylamine (0.06 g), tetrahydrofuran and NaOH 1N (0.00067 mol). The reaction mixture was stirred for 3 days at room temperature, then for 1 day at 75° C., for 1 day at 90° C. and for 2 days at 110° C. To O-methylhydroxylamine (0.60 g) was added tetrahydrofuran (4 ml) and NaOH 50% (0.00719 mol). The liquid was decanted into the reaction flask and the reaction mixture was heated at 110° C. for 3 days. The solvent was evaporated. The residue was dissolved in CH₂Cl₂, washed with a saturated NaHCO₃ solution and water, dried (Na₂SO₄), filtered and the solvent was evaporated. The residue was purified by column chromatography over silica gel (eluent: CH₂Cl₂/CH₃OH 98/2). The pure fractions were collected and the solvent was evaporated. The residue was crystallized from CH₃CN, filtered off and dried, yielding 0.15 g of 4-[[5-bromo-4-(4-cyano-2,6-dimethylphenoxy)-6-(methoxyamino)-2-pyrimidinyl]amino]benzonitrile (51%); mp. 185-186° C. The sample was dried (0.2 mm Hg, 80° C., 16 hours) (comp. 48).

Example B17 a) n-Butyllithium (2.0 l, 0.005 mol) was added to a 0° C. stirred solution of 1-(methylethyl)-2-propanamine (0.70 ml, 0.005 mol) and tetrahydrofuran (300 ml). After stirring cold for 30 min, compound (17) (0.005 mol) was added. The resulting mixture was stirred cold for 30 min at which point 1,1-dimethylethyl bromoacetate (1.5 ml, 10 mmol) was added and the temperature was allowed to rise to room temperature and the reaction was stirred for three. In a separate flask n-butyllithium (2.0 ml, 5 mmol) was added to a stirred 0° C. solution of 1-(methylethyl)-2-propanamine (0.70 ml, 5 mmol) in tetrahydrofuran (50 ml) and allowed to react for 30 min at which time it was transferred to the room temperature reaction. This procedure was repeated. Quenched with 0.5 ml H₂O, the sample was concentrated by rotary evaporation onto silica gel, and purified by flash chromatography (eluting with 0, 10, 20% ethylacetate in hexanes) to give a white solid of

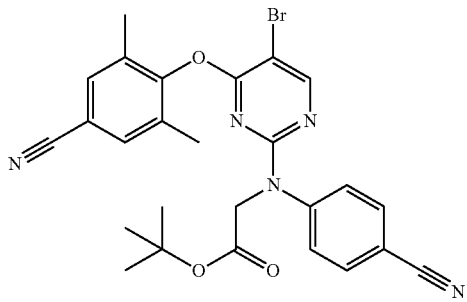 [SMILES: Cc1cc(C#N)cc(C)c1Oc1nc(N(CC(=O)OC(C)(C)C)c2ccc(C#N)cc2)ncc1Br]

mp. 195-197° C. (comp. 56).

b) A suspension of compound (17) in 40 ml of N,N-dimethylformamide was treated with 0.24 g of NaH. The effervescent mixture was stirred for 90. A solution of 1,4-dichloro-1,4-butanedione in 10 ml N,N-dimethylformamide was prepared and cooled in an ice bath. The mixture prepared from compound (17) was transferred to the cold solution of 1(methylethyl)-1-propanamine and was warmed to room temperature with stirring for 42 hours. Another 0.24 g of NaH was added, the reaction was stirred for 3 days, and diluted with ether and poured into ice. Precipitation was removed by filtration. The 2 phase filtrate was separated and the acidic aqueous fraction was extracted twice more with ether. The combined ether fractions were washed with small volumes of distilled water and dried. The solvent was evaporated and the residue was subjected to silica gel column chromatography. Reverse phase prep HPLC with immediate cooling for lyophilization of the appropriate fractions provided 0.07 g of

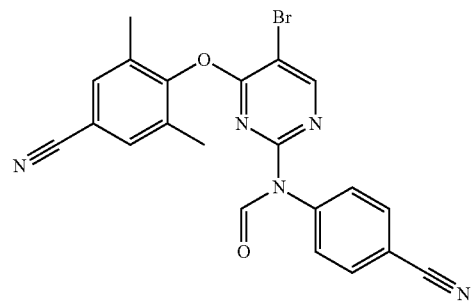 [SMILES: Cc1cc(C#N)cc(C)c1Oc1nc(N(C=O)c2ccc(C#N)cc2)ncc1Br]

(7.8%); mp. 232-233° C. (comp. 57).

c) To a flask under argon was added NaH 60% and tetrahydrofuran. The reaction was stirred at room temperature for 10 min and compound (17) added. After stirring for 1 hr ethyl carbonochloridate was added. The reaction mixture was stirred at room temperature for another 16 hrs and the solvent evaporated. The residue was partially dissolved in dimethylsulfoxide and filtered. The filtrate was purified by reverse phase chromatography and lyophilized to give 0.47 g (18%) of

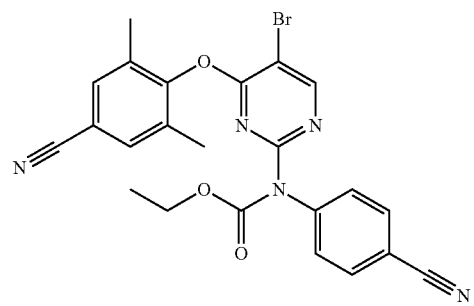 [SMILES: CCOC(=O)N(c1ccc(C#N)cc1)c1ncc(Br)c(Oc2c(C)cc(C#N)cc2C)n1]

(comp. 58).

d) A mixture of 4-[[5-amino-4-(4-cyano-2,6-dimethylphenoxy)-2-pyrimidinyl]amino]benzonitrile (0.00147 mol) in ethanoic acid anhydride (10 ml) and 2-propanone (10 ml) was stirred at room temperature for 16 hours. The mixture was then heated to 55° C., and more ethanoic acid anhydride (3 ml) was added. The mixture was removed from heat after 18 hours and stirred for 6 days at room temperature. The sample was concentrated by rotary evaporation to a solid. Purification by column chromatography (eluting with 0, 0.5, 1, 1.5, 2% (10% NH₄OH in CH₃OH) in methylene chloride) yielded;

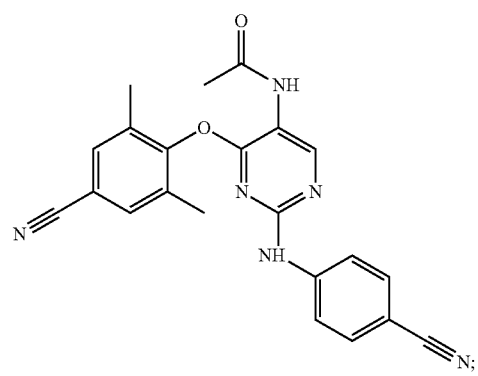 [SMILES: CC(=O)Nc1cnc(Nc2ccc(C#N)cc2)nc1Oc1c(C)cc(C#N)cc1C]

mp. 290-295° C. The solid was dried in vacuo for 16 hours at 60° C. (comp. 49).

Example B18

A mixture of 4-[[4-(4-cyano-2,6-dimethylphenoxy)-5-nitro-2-pyrimidinyl]amino]benzonitrile (0.0005 mol) in tetrahydrofuran (20 ml) was hydrogenated overnight with Pd/C 10% (0.100 g) as a catalyst. After uptake of $H_2$ (3 equiv; 0.0015 mol), the catalyst was filtered off and the filtrate was concentrated by rotary evaporation and dried in vacuo over 16 hours at 40° C., yielding 0.15 g of 4-[[5-amino-4-(4-cyano-2,6-dimethylphenoxy)-2-pyrimidinyl]amino]benzonitrile (84%); mp. >300° C. (comp. 50).

Example B19

4-[[4-[(2,4,6-trimethylphenyl)amino]-5-nitro-2-pyrimidinyl]amino]benzonitrile (0.001 mol), Pd/C 10% (0.025 g), ethanol (20 ml), and hydrazine (0.030 mol) were combined to form a slurry and stirred at room temperature for 16 hours. The solvent was removed by rotary evaporation. The residue was taken up in tetrahydrofuran (20 ml) and methanol (1 ml). A second portion of hydrazine (0.5 g) was added, and the reaction was stirred for 16 hours at room temperature. A third portion of hydrazine (0.5 ml) was added and the reaction was stirred for an additional 16 hours at room temperature. The sample was concentrated by rotary evaporation onto silica gel (1 g) and purified by flash chromatography (eluent: 0.5, 1, 2% 10% ($NH_4OH$ in $CH_3OH$) in $CH_2Cl_2$). The desired fractions were purified by preparatory HPLC to yield 0.24 g of 4-[[5-amino-4-[(2,4,6-trimethylphenyl)amino]-2-pyrimidinyl]amino]benzonitrile (70%); mp. 224-225° C. (comp. 51).

Example B20

Compound (3) (0.001 mol), trimethyl silanecarbonitrile (0.0012 mol), Pd(PPh$_3$)$_2$Cl$_2$ (0.020 g), CuI (0.010 g) and CF$_3$COOH/H$_2$O (3 ml) were combined in a sealed tube and heated to 110° C. for 10 hours. Second portions of the catalysts Pd(PPh$_3$)$_2$Cl$_2$ (0.020 g) and CuI (0.010 g), and CF$_3$COOH/H$_2$O (3 ml) were added and the reaction mixture was stirred for 10 hours at 110° C. The material was concentrated by rotary evaporation. The residue was purified by preparative reversed-phase HPLC. The desired fractions were concentrated and purified by reversed-phase preparative HPLC and dried with a stream of $N_2$, then in vacuo at 40° C. for 16 hours. Yield: 0.011 g of 4-[[5-ethynyl-4-[(2,4,6-trimethylphenyl)amino]-2-pyrimidinyl]amino]benzonitrile; mp. 165-175° C. (comp. 52).

Example B21

Compound (3) (0.000906 mol), tributylphenyl stannane (0.000906 mol), Pd(PPh$_3$)$_4$ (0.002718 mol), and 1,4-dioxane (3 ml) were combined under $N_2$ in a sealed tube and heated to 110° C. for 16 hours. The reaction mixture was cooled and concentrated by rotary evaporation. The sample was purified by Preparatory Reverse Phase HPLC, then dried under Ar stream. Drying in vacuo yielded 0.0845 g of or 4-[[5-phenyl-4-[(2,4,6-trimethylphenyl)amino]-2-pyrimidinyl]amino]benzonitrile; mp. 209-214° C. (comp. 53).

Example B22

Compound (3) (0.001 mol), tetraethenyl stannane (0.22 ml), 1,4-dioxane (2 ml) and Pd(PPh$_3$)$_4$ (0.112 g) were combined in a sealed tube under Ar. The mixture was stirred and heated to 100° C. for 16 hours. More tetraethenyl stannane and Pd(PPh$_3$)$_4$ were added. The reaction was placed under Ar, stirred and heated. The reaction was concentrated by rotary evaporation and purified on preparative HPLC. The material was dried with a $N_2$ stream, and dried under vacuum for 4 hours at 60° C. to obtain 0.422 g of 4-[[5-ethenyl-4-[(2,4,6-trimethylphenyl)amino]-2-pyrimidinyl]amino]benzonitrile; mp. 237-242° C. (comp. 54).

Example B23

Compound (3) (0.001225 mol), CuCN (0.001470 mol) and N,N-dimethylformamide (2 ml) were combined in a sealed tube under Argon, then stirred and heated to 160° C. for 16 hours. The residue was purified by column chromatography (eluent: $CH_2Cl_2$/hexane 1/1, then pure $CH_2Cl_2$). The desired fractions were collected and the solvent was evaporated. The residue was triturated under $CH_2Cl_2$ at room temperature. The solid was dried (vacuum, 40° C., 24 hours, yielding 0.0864 g of

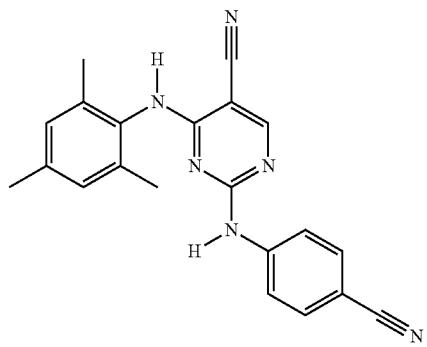 [SMILES: Cc1cc(C)c(Nc2nc(Nc3ccc(C#N)cc3)ncc2C#N)c(C)c1]

(24%); mp. 254-259° C. (comp .55). Tables 1, 2, 3 and 4 list compounds of formula (I-a) which were made analogous to one of the above examples.

TABLE 1

| Comp. No. | Ex. No. | Y | Physical data |
|---|---|---|---|
| 1 | B1a | Cl | — |
| 2 | B1a | Br | mp. 227-228° C. |
| 22 | B11 | NO$_2$ | mp. 224-226° C. |

TABLE 2

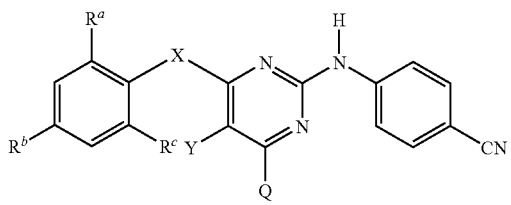

| Co. No. | Ex. No. | $R^a$ | $R^b$ | $R^c$ | X | Y | Q | mp./salt |
|---|---|---|---|---|---|---|---|---|
| 3 | B1b | CH₃ | CH₃ | CH₃ | NH | Br | H | mp. 227-228° C. |
| 4 | B2 | CH₃ | CH₃ | CH₃ | NH | Cl | NH₂ | mp. 241-242° C.; trifluoroacetate (1:1) |
| 5 | B3 | CH₃ | CH₃ | CH₃ | NH | Cl | H | mp. 224-226° C. |
| 6 | B5 | CH₃ | CH₃ | CH₃ | O | Cl | H | mp. 218-219° C. |
| 7 | B5 | CH₃ | CH₃ | CH₃ | S | Cl | H | mp. 264-266° C. |
| 8 | B5 | CH₃ | Br | CH₃ | O | Cl | H | mp. 237-238° C. |
| 9 | B3 | CH₃ | Br | CH₃ | NH | Cl | H | mp. 217-219° C. |
| 10 | B4 | Br | CH₃ | Br | NH | Cl | H | mp. 262-263° C. |
| 11 | B4 | Br | Br | F | NH | Cl | H | mp. 200-202° C. |
| 12 | B4 | CH₃ | C(CH₃)₃ | CH₃ | NH | Cl | H | mp. 214-215° C. |
| 13 | B4 | CH₃ | CN | CH₃ | NH | Cl | H | mp. 281-283° C. |
| 14 | B4 | Cl | Cl | CH₃ | NH | Cl | H | mp. 243-245° C. |
| 15 | B5 | Cl | Br | CH₃ | O | Cl | H | mp. 244-247° C. |
| 16 | B5 | CH₃ | Cl | CH₃ | O | Cl | H | mp. 232-235° C. |
| 17 | B6 | CH₃ | CN | CH₃ | O | Br | H | mp. 288-289° C. |
| 18 | B5 | CH₃ | CN | CH₃ | O | Cl | H | mp. 283-284° C. |
| 19 | B7 | CH₃ | CN | CH₃ | NH | Cl | NH₂ | mp. 266-268° C. trifluoroacetate (1:1) |
| 20 | B3 | Cl | Cl | CH₃ | NH | Br | H | mp. 253-254° C. |
| 21 | B3 | CH₃ | Br | CH₃ | NH | Br | H | mp. 243-245° C. |
| 23 | B23 | CH₃ | CN | CH₃ | NH | CN | H | mp. 275-290° C. trifluoroacetate (1:1) |
| 24 | B23 | CH₃ | Br | CH₃ | NH | CN | H | mp. 291-299° C. |
| 25 | B14 | CH₃ | CN | CH₃ | O | Br | NH—CH₃ | mp. 248-250° C. |
| 26 | B14 | CH₃ | CN | CH₃ | O | Br | NH₂ | mp. 255-256° C. |
| 27 | B14 | CH₃ | CH₃ | CH₃ | O | Br | NH₂ | — |
| 28 | B14 | CH₃ | CH₃ | CH₃ | O | Br | NH—CH₃ | mp. 213-214° C. |
| 29 | B14 | CH₃ | CN | CH₃ | O | Br | NH—C₂H₅ | mp. 263-264° C. |
| 30 | B14 | CH₃ | CN | CH₃ | O | Cl | NH₂ | mp. 272-274° C. |
| 31 | B14 | CH₃ | CH₃ | CH₃ | O | Cl | NH₂ | mp. 199-202° C. |
| 32 | B11 | CH₃ | CH₃ | CH₃ | NH | NO₂ | H | mp. >300° C. |
| 33 | B5 | CH₃ | CH₃ | CH₃ | O | Br | H | mp. 207-215° C. |
| 34 | B5 | CH₃ | CH₃ | CH₃ | O | Cl | Cl | mp. 225-226° C. |
| 35 | B5 | CH₃ | CN | CH₃ | O | Cl | Cl | mp. 273-276° C. |
| 36 | B6 | CH₃ | CN | CH₃ | O | Cl | Br | mp. 281-282° C. |
| 37 | B7 | CH₃ | CH₃ | CH₃ | O | Cl | Br | mp. 214-215° C. |
| 40 | B8 | CH₃ | CH(CH₃)₂ | CH₃ | NH | Br | H | mp. 198° C. trifluoroacetate (1:2) |
| 41 | B10 | CH₃ | CH₃ | CH₃ | NH | Br | Cl | mp. 220° C. |
| 42 | B9 | CH₃ | CN | CH₃ | NH | Br | Cl | mp. 259° C. |
| 43 | B11 | CH₃ | CN | CH₃ | O | NO₂ | H | mp. >300° C. |
| 44 | B12 | CH₃ | CN | CH₃ | O | Br | CH₃ | mp. 260° C. |
| 45 | B13 | CH₃ | CN | CH₃ | NH | Br | H | mp. 277° C. |
| 46 | B14 | CH₃ | CN | CH₃ | O | Br | NH₂ | mp. 255° C. |
| 47 | B15 | CH₃ | CN | CH₃ | O | Br | ![NH-CH₂CH₂-pyrrolidinyl] | mp. 208° C.; HCl (1:1) |
| 48 | B16 | CH₃ | CN | CH₃ | O | Br | —NH—O—CH₃ | mp. 185-186° C. |
| 49 | B17d | CH₃ | CN | CH₃ | O | —NH—COCH₃ | H | mp. 290-295° C. |
| 50 | B18 | CH₃ | CN | CH₃ | O | —NH₂ | H | mp. >300° C. |
| 51 | B18 | CH₃ | CH₃ | CH₃ | NH | —NH₂ | H | mp. 224-225° C.; trifluoroacetate (1:1) |
| 52 | B20 | CH₃ | CH₃ | CH₃ | NH | CN | H | mp. 165-175° C. |
| 53 | B21 | CH₃ | CH₃ | CH₃ | NH | phenyl | H | mp. 209-214° C. |
| 54 | B22 | CH₃ | CH₃ | CH₃ | NH | —CH=CH₂ | H | mp. 237-242° C.; trifluoroacetate (1:1) |
| 55 | B23 | CH₃ | CH₃ | CH₃ | NH | —CH=CH₂ | H | mp. 254-259° C. |

TABLE 3

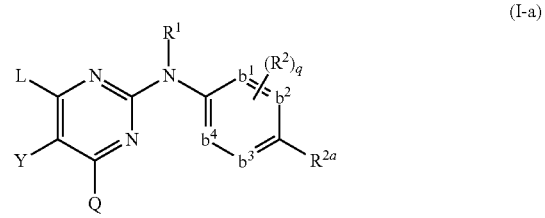

| Comp. No. | Ex. No. | Z | |
|---|---|---|---|
| 38 | B17C | —C(=O)—CH$_3$ | mp. 194-196° C. |
| 56 | B17a | —CH$_2$—CO—O—C(CH$_3$)$_3$ | mp. 195-197° C. |
| 57 | B17b | —CH=O | mp. 232-233° C. |
| 58 | B17e | —CO—O—C$_2$H$_5$ | mp. 209-210° C. |
| 59 | B6b | —CH$_2$—CO—OC$_2$H$_5$ | mp. 185-190° C. |
| 60 | B6c | —CH$_2$—O—CO—C(CH$_3$)$_3$ | mp. 168-169° C. |
| 61 | Bbd | —CO—CH$_2$—OCH$_2$—CO—OCH$_3$ | mp. 184-185° C. |

TABLE 4

| Comp. No. | Ex. No. | R$^a$ | R$^b$ | X | Y | Q | |
|---|---|---|---|---|---|---|---|
| 39 | B5 | Cl | Cl | S | Br | H | mp. 198-200° C. |

C. Pharmacological Example

Example C.1

A rapid, sensitive and automated assay procedure was used for the in vitro evaluation of anti-HIV agents. An HIV-1 transformed T4-cell line, MT-4, which was previously shown (Koyanagi et al., *Int. J. Cancer*, 36, 445-451, 1985) to be highly susceptible to and permissive for HIV infection, served as the target cell line. Inhibition of the HIV-induced cytopathic effect was used as the end point. The viability of both HIV- and mock-infected cells was assessed spectrophotometrically via the in situ reduction of 3-(4,5-dimethylthiazol-2-yl)-2,5-diphenyltetrazolium bromide (MTT). The 50% cytotoxic concentration (CC$_{50}$ in µM) was defined as the concentration of compound that reduced the absorbance of the mock-infected control sample by 50%. The percent protection achieved by the compound in HIV-infected cells was calculated by the following formula:

$$\frac{(OD_T)_{HIV} - (OD_C)_{HIV}}{(OD_C)_{MOCK} - (OD_C)_{HIV}} \text{ expressed in \%,}$$

whereby $(OD_T)_{HIV}$ is the optical density measured with a given concentration of the test compound in HIV-infected cells; $(OD_C)_{HIV}$ is the optical density measured for the control untreated HIV-infected cells; $(OD_C)_{MOCK}$ is the optical density measured for the control untreated mock-infected cells; all optical density values were determined at 540 nm. The dose achieving 50% protection according to the above formula was defined as the 50% inhibitory concentration (IC$_{50}$ in µM). The ratio of CC$_{50}$ to IC$_{50}$ was defined as the selectivity index (SI). The compounds of formula (I-A) were shown to inhibit HIV-1 effectively. Particular IC$_{50}$, CC$_{50}$ and SI values are listed in Table 5 hereinbelow.

TABLE 5

| Co. No. | IC$_{50}$ (µM) | CC$_{50}$ (µM) | SI | Co. No. | IC$_{50}$ (µM) | CC$_{50}$ (µM) | SI |
|---|---|---|---|---|---|---|---|
| 2 | 0.030 | 82.6 | 2730 | 10 | 0.005 | 0.4 | 92 |
| 3 | 0.006 | 4.4 | 738 | 11 | 0.002 | 0.4 | 183 |
| 1 | 0.004 | 10.9 | 2787 | 12 | 0.020 | 48.5 | 2393 |
| 4 | 0.002 | 10.0 | 5555 | 13 | 0.0005 | 0.4 | 860 |
| 5 | 0.002 | 0.4 | 178 | 14 | 0.002 | 0.4 | 191 |
| 6 | 0.009 | >100 | >11049 | 15 | 0.010 | >100 | >9661 |
| 7 | 0.084 | >100 | >1182 | 16 | 0.010 | >100 | >10416 |
| 8 | 0.012 | >100 | >8298 | 17 | 0.002 | >10 | >6451 |
| 9 | 0.003 | 1.2 | 376 | 18 | 0.001 | >10 | >7142 |
| 46 | 0.002 | >200 | >71428 | 60 | 0.002 | 74.52 | 39223 |
| 61 | 0.002 | >100 | >52631 | | | | |

The invention claimed is:

1. A compound having the formula

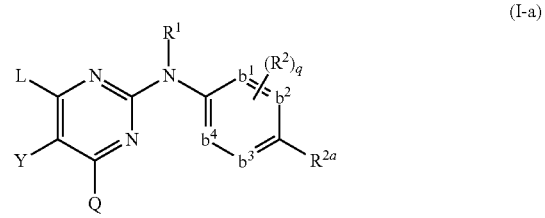

(I-a)

a N-oxide, an addition salt, or a stereochemically isomeric form thereof, wherein -b$^1$=b$^2$-C(R$^{2a}$)=b$^3$-b$^4$= represents a bivalent radical of formula

—N=CH—C(R$^{2a}$)=CH—CH=  (b-2);

—CH=N—C(R$^{2a}$)=CH—CH=  (b-3);

—N=CH—C(R$^{2a}$)=N—CH=  (b-4);

—N=CH—C(R$^{2a}$)=CH—N=  (b-5);

—CH=N—C(R$^{2a}$)=N—CH=  (b-6);

—N=N—C(R$^{2a}$)=CH—CH=  (b-7);

q is 0, 1, 2 or 3;

R$^1$ is hydrogen; aryl; formyl; C$_{1-6}$alkylcarbonyl; C$_{1-6}$alkyl; C$_{1-6}$alkyloxycarbonyl; C$_{1-6}$alkyl substituted with formyl, C$_{1-6}$alkylcarbonyl, C$_{1-6}$alkyloxycarbonyl, C$_{1-6}$alkylcarbonyloxy; C$_{1-6}$alkyloxyC$_{1-6}$alkylcarbonyl substituted with C$_{1-6}$alkyloxycarbonyl;

R$^{2a}$ is cyano, aminocarbonyl, mono- or di(methyl)aminocarbonyl, C$_{1-6}$alkyl substituted with cyano, aminocarbonyl or mono- or di(methyl)aminocarbonyl, C$_{2-6}$alkenyl substituted with cyano, or C$_{2-6}$alkynyl substituted with cyano;

each R$^2$ independently is hydroxy, halo, C$_{1-6}$alkyl optionally substituted with cyano or —C(=O)R$^6$, C$_{3-7}$cycloalkyl, C$_{2-6}$alkenyl optionally substituted with one or more halogen atoms or cyano, C$_{2-6}$alkynyl optionally substituted with one or more halogen atoms or cyano, C$_{1-6}$alkyloxy, C$_{1-6}$alkyloxycarbonyl, carboxyl, cyano, nitro, amino, mono- or di(C$_{1-6}$alkyl)amino, polyhalomethyl, polyhalomethyloxy, polyhalomethylthio, —S(=O)$_p$R$^6$, —NH—S(=O)$_p$R$^6$, —C(=O)R$^6$, —NHC(=O)H, —C(=O)NHNH$_2$, —NHC(=O)R$^6$, —C(=NH)R$^6$ or a radical of formula

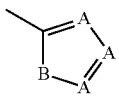

(c)

wherein each A independently is N, CH or CR$^6$;
B is NH, O, S or NR$^6$;
p is 1 or 2; and
R$^6$ is methyl, amino, mono- or dimethylamino or polyhalomethyl;

L is C$_{1-10}$alkyl, C$_{2-10}$alkenyl, C$_{2-10}$alkynyl, C$_{3-7}$cycloalkyl, whereby each of said aliphatic group may be substituted with one or two substituents independently selected from
C$_{3-7}$cycloalkyl,
indolyl or isoindolyl, each optionally substituted with one, two, three or four substituents each independently selected from halo, C$_{1-6}$alkyl, hydroxy, C$_{1-6}$alkyloxy, cyano, aminocarbonyl, nitro, amino, polyhalomethyl, polyhalomethyloxy and C$_{1-6}$alkylcarbonyl,
phenyl, pyridinyl, pyrimidinyl, pyrazinyl or pyridazinyl, wherein each of said aromatic rings may optionally be substituted with one, two, three, four or five substituents each independently selected from the substituents defined in R$^2$; or L is —X—R$^3$ wherein
R$^3$ is phenyl, pyridinyl, pyrimidinyl, pyrazinyl or pyridazinyl, wherein each of said aromatic rings may optionally be substituted with one, two, three, four or five substituents each independently selected from the substituents defined in R$^2$; and
X is —NR$^1$—, —NH—NH—, —N=N—, —O—, —C(=O)—, —CHOH—, —S—, —S(=O)— or —S(=O)$_2$—;
Q represents hydrogen, C$_{1-6}$alkyl, halo, polyhaloC$_{1-6}$alkyl or —NR$^4$R$^5$; and
R$^4$ and R$^5$ are each independently selected from hydrogen, hydroxy, C$_{1-12}$alkyl, C$_{1-12}$alkyloxy, C$_{1-12}$alkylcarbonyl, C$_{1-12}$alkyloxycarbonyl, aryl, amino, mono- or di(C$_{1-12}$alkyl)amino, mono- or di(C$_{1-12}$alkyl)aminocarbonyl wherein each of the aforementioned C$_{1-12}$alkyl groups may optionally and each individually be substituted with one or two substituents independently selected from hydroxy, C$_{1-6}$alkyloxy, hydroxyC$_{1-6}$alkyloxy, carboxyl, C$_{1-6}$alkyloxycarbonyl, cyano, amino, imino, mono- or di(C$_{1-6}$alkyl)amino, polyhalomethyl, polyhalomethyloxy, polyhalomethylthio, —S(=O)$_p$R$^6$, —NH—S(=O)$_p$R$^6$, —C(=O)R$^6$, —NHC(=O)H, —C(=O)NHNH$_2$, —NHC(=O)R$^6$, —C(=NH)R$^6$, aryl and Het; or
R$^4$ and R$^5$ taken together may form pyrrolidinyl, piperidinyl, morpholinyl, azido or mono- or di(C$_{1-12}$alkyl)aminoC$_{1-4}$-alkylidene;
Y represents hydroxy, halo, C$_{3-7}$cycloalkyl, C$_{2-6}$alkenyl optionally substituted with one or more halogen atoms, C$_{2-6}$alkynyl optionally substituted with one or more halogen atoms, C$_{1-6}$alkyl substituted with cyano or —C(=O)R$^6$, C$_{1-6}$alkyloxy, C$_{1-6}$alkyloxycarbonyl, carboxyl, cyano, nitro, amino, mono- or di(C$_{1-6}$alkyl)amino, polyhalomethyl, polyhalomethyloxy, polyhalomethylthio, —S(=O)$_p$R$^6$, —NH—S(=O)$_p$R$^6$, —C(=O)R$^6$, —NHC(=O)H, —C(=O)NHNH$_2$, —NHC(=O)R$^6$, —C(=NH)R$^6$ or aryl;
aryl is phenyl or phenyl substituted with one, two, three, four or five substituents each independently selected from halo, C$_{1-6}$alkyl, C$_{3-7}$cycloalkyl, C$_{1-6}$alkyloxy, cyano, nitro, polyhaloC$_{1-6}$alkyl and polyhaloC$_{1-6}$alkyloxy;
Het is an aliphatic or aromatic heterocyclic radical; said aliphatic heterocyclic radical is selected from pyrrolidinyl, piperidinyl, homopiperidinyl, piperazinyl, morpholinyl, tetrahydrofuranyl and tetrahydrothienyl wherein each of said aliphatic heterocyclic radical may optionally be substituted with an oxo group; and said aromatic heterocyclic radical is selected from pyrrolyl, furanyl, thienyl, pyridinyl, pyrimidinyl, pyrazinyl and pyridazinyl wherein each of said aromatic heterocyclic radical may optionally be substituted with hydroxy.

2. A compound as claimed in claim 1 wherein R$^1$ is hydrogen, aryl, formyl, C$_{1-6}$alkylcarbonyl, C$_{1-6}$alkyl, C$_{1-6}$alkyloxycarbonyl, C$_{1-6}$alkyl substituted with formyl, C$_{1-6}$alkylcarbonyl, C$_{1-6}$alkyloxycarbonyl.

3. A compound as claimed in claim 1 wherein L is —X—R$^3$ wherein R$^3$ is 2,4,6-trisubstituted phenyl.

4. A compound as claimed in claim 1 wherein Y is cyano, —C(=O)NH$_2$ or a halogen.

5. A compound as claimed in claim 1 wherein Q is hydrogen or NR$^4$R$^5$.

6. A pharmaceutical composition comprising a pharmaceutically acceptable carrier and a therapeutically active amount of a compound as claimed in claim 1.

7. A process for preparing a compound as claimed in claim 1, comprising
a) reacting an intermediate of formula (II) with an amino derivative of formula (III) under solvent-free conditions or in a reaction-inert solvent under a reaction-inert atmosphere

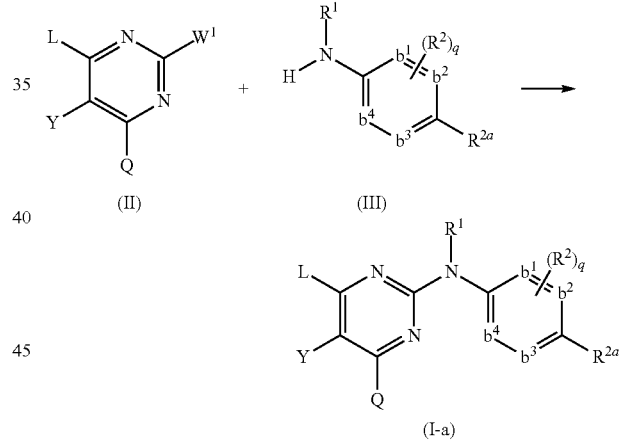

wherein W$^1$ is a suitable leaving group and L, Y, Q, R$^1$, R$^2$, R$^{1a}$, q and -b$^1$=b$^2$-C(R$^{2a}$)=b$^3$-b$^4$= are as defined in claim 1;
b) reacting an intermediate of formula (IV) with an intermediate of formula (V) under solvent-free conditions or in an appropriate solvent under a reaction-inert atmosphere

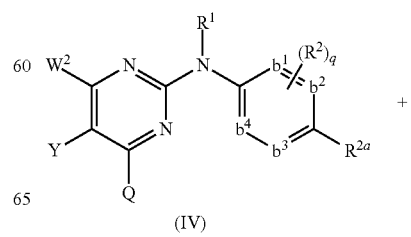

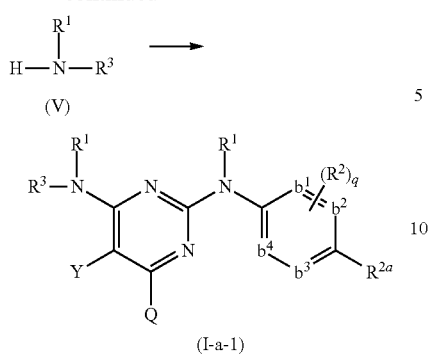

(V)

(I-a-1)

wherein $W^2$ is a suitable leaving group and Y, Q, $R^1$, $R^2$, $R^{2a}$, $R^3$, q and $-b^1=b^2-C(R^{2a})=b^3-b^4=$ are as defined in claim 1;

c) reacting an intermediate of formula (IV) with an intermediate of formula (VI) in an appropriate solvent under a reaction-inert atmosphere in the presence of a suitable base

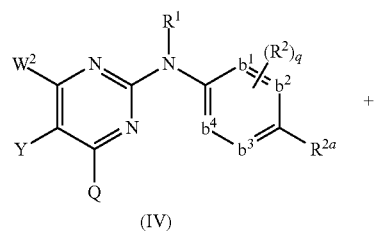

(IV)

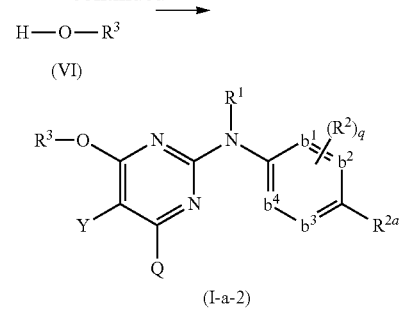

(VI)

(I-a-2)

wherein $W^2$ is a suitable leaving group and Y, Q, $R^1$, $R^2$, $R^{2a}$, $R^3$, q and $-b^1=b^2-C(R^{2a})=b^3-b^4=$ are as defined in claim 1;

or optionally converting compounds of formula (I-a) into each other following art-known transformation reactions; and further, if desired, converting the compounds of formula (I-a), into an acid addition salt by treatment with an acid, or conversely, converting the acid addition salt form into the free base by treatment with alkali; and optionally preparing stereochemically isomeric forms thereof.

8. The combination of a compound as defined in claim 1 and another antiretroviral compound.

9. A product containing (a) a compound as defined in claim 1 and (b) another antiretroviral compound, as a combined preparation for simultaneous, separate or sequential use in anti-HIV treatment.

10. A pharmaceutical composition comprising a pharmaceutically acceptable carrier and as active ingredients (a) a compound as defined in claim 1 and (b) another antiretroviral compound.

* * * * *